US007440599B2

(12) United States Patent
Kato

(10) Patent No.: US 7,440,599 B2
(45) Date of Patent: Oct. 21, 2008

(54) APPARATUS AND METHOD FOR PROCESSING X-RAY IMAGES

(75) Inventor: Hisanori Kato, Tochigi-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 973 days.

(21) Appl. No.: 10/627,812

(22) Filed: Jul. 28, 2003

(65) Prior Publication Data

US 2004/0114717 A1 Jun. 17, 2004

(30) Foreign Application Priority Data

Jul. 29, 2002 (JP) ............................. 2002-220203

(51) Int. Cl.
*G06K 9/00* (2006.01)
(52) U.S. Cl. ...................... 382/128; 382/130; 382/131; 382/132; 382/284; 382/294
(58) Field of Classification Search ................ 382/128, 382/130, 131, 132, 284, 294
See application file for complete search history.

(56) References Cited

U.S. PATENT DOCUMENTS

| | | | | |
|---|---|---|---|---|
| 5,123,056 | A * | 6/1992 | Wilson | 382/132 |
| 6,078,699 | A * | 6/2000 | Lobregt et al. | 382/284 |
| 6,459,094 | B1 * | 10/2002 | Wang et al. | 250/584 |
| 6,563,943 | B1 * | 5/2003 | Sasada | 382/132 |
| 6,714,680 | B1 * | 3/2004 | Sasada | 382/216 |
| 6,904,164 | B2 * | 6/2005 | Norioka et al. | 382/145 |
| 6,961,478 | B2 * | 11/2005 | Inoue | 382/284 |
| 7,123,779 | B2 * | 10/2006 | Beuker et al. | 382/294 |
| 7,127,090 | B2 * | 10/2006 | Kreang-Arekul et al. | 382/128 |
| 7,162,102 | B2 * | 1/2007 | Cahill et al. | 382/288 |
| 2003/0138137 | A1 * | 7/2003 | Bojer et al. | 382/132 |

* cited by examiner

*Primary Examiner*—Bhavesh Mehta
*Assistant Examiner*—John B Strege
(74) *Attorney, Agent, or Firm*—Oblon, Spivak, McClelland, Maier & Neustadt, P.C.

(57) ABSTRACT

An X-ray image processing apparatus and method for processing X-ray images for generating a continuous X-ray image of relatively uniform converted gradations by pasting a plurality of consecutive divisional X-ray images. The plurality of consecutive divisional X-ray images are obtained along an examining body. Each of the consecutive divisional X-ray images is overlapped at its edge with an adjoining image. An index value for the respective divisional X-ray images is calculated based on pixel values in the overlapped portion between the images. Each of pixel values for the respective plurality of consecutive divisional X-ray images is adjusted or corrected so as to be relatively uniform to an index value for an adjoining divisional image. The gradation corrected divisional images are pasted together in order to produce the continuous image.

32 Claims, 17 Drawing Sheets

APPARATUS AND METHOD FOR PROCESSING X-RAY IMAGES

CROSS-REFERENCE TO RELATED APPLICATIONS

This application claims the benefit of priority from Japanese Patent Application No. 2002-220203, filed on Jul. 29, 2002, which is hereby incorporated by reference in its entirety.

BACKGROUND OF THE INVENTION

1. Field of the Invention

The present invention relates to an apparatus and method for processing X-ray images, and more particularly to an apparatus and method for generating a continuous X-ray image of a relatively uniform density.

2. Description of the Related Art

X-ray image processing apparatuses are applicable to medical and industrial uses. Generally, in an X-ray image processing apparatus, X-ray radiation is emitted from an X-ray tube passing over an examining body, e.g., a patient, and is detected by an X-ray detector provided so as to face the X-ray tube. The detector converts X-ray data that penetrates through the examining body into analog electrical signals. The resulting electrical signals are converted to digital image data through an analog/digital (A/D) converter provided in the X-ray image processing apparatus. The digital image data are used for various image processing in the X-ray image apparatus. The processed digital image data are displayed on a monitor as X-ray density images or printed on a film by a laser imager. It is possible to store the processed digital image data in a storage medium provided in the apparatus or in an external storage medium. Further it is possible to transfer digital image data from the image processing apparatus to remote equipment through networks.

Generally, an X-ray diaphragm is attached to an exit window of an X-ray tube. Thus, the X-ray tube and the X-ray diaphragm constitute an X-ray generating device. The X-ray generating device and a detector are interlocked through a linked motion frame so as to move while keeping a linked position. The linked motion frame is movably supported by rails provided on a ceiling of an inspection room or by a bed frame in order to move the interlocked devices in a wide range from the top to the end of an examining body without moving the examining body.

Such a wide rage of movement of the interlocked pair of an X-ray generating device and a detector for obtaining X-ray images at various positions is used for, as one example, in lower legs angiography as an X-ray image diagnosis. For the lower legs angiography, a wide range X-ray image is needed from the abdomen of a patient to his feet tips while following an injected contrast agent. However, at present, there is no X-ray radiating and X-ray detecting equipment that can cover such a wide range at once. Accordingly, it has been proposed to obtain X-ray images of such a wide range by dividing the whole area into a plurality of consecutive divisional areas. Thus, once after injecting a contrast agent from a patient abdomen, a plurality of divisional X-ray images are obtained while following the injected contrast agent ridden on an aorta blood flow from the abdomen to the feet tips in order to avoid extreme burden for a patient.

For performing such divisional X-ray imaging, there are two types of methods including a stepping method and the bolus chase method. The stepping method repeats intermittent operations of X-ray imaging, stopping and movement by the pair of the X-ray generating device and detector. Namely, when the linked pair of the X-ray generating device and the detector has completed an X-ray imaging operation at a position for detecting a contrast enhancing agent, the pair is quickly moved to a next imaging position at a faster speed than the flowing speed of the contrast enhancing agent and stays until the contrast enhancing agent arrives to that imaging position. The pair performs an X-ray imaging operation at an arrival time of the contrast enhancing agent to the position. By repeating such intermittent operations, a plurality of divisional X-ray imaging covers the whole of the examining area of a wide range. The bolus chase method performs divisional X-ray imaging operations by consecutively moving the linked pair of the X-ray generating device and detector while chasing the flow of the contrast enhancing agent. Thus, the X-ray imaging operation is always completed during the movement of the linked pair of X-ray generating device and detector. For lower legs angiography, a plurality of divisional X-ray images obtained by these methods are pasted so as to generate a continuous whole image of blood vessel of a wide range from a patient abdomen to his foot tips.

However, when such divisional X-ray imaging operations are repeated in such a wide range for lower legs angiography, the detected amounts of X-rays penetrated through a patient are largely varied due to influences of body thickness and bones in the patient, or due to directly incident X-rays that do not penetrate the patient body. Consequently, for the lower legs angiography to perform the divisional X-ray imaging operation, the X-ray amount needs to be changed at every position for the divisional imaging operation. When the X-ray amounts are changed at each imaging position, a large variation of pixel values appear among the plurality of divisional X-ray images. Thus, when such divisional X-ray images of varied pixel values are pasted for generating a continuous image, it lacks continuity due to the density variation among the divisional X-ray images. Thus, the deficiency of density continuity in the continuous image makes diagnosis difficult. Especially, when the bolus chase method is applied, an X-ray imaging operation needs to be performed in a very short time in order to avoid shading off of images due to the constant movement of the linked pair of the X-ray generating device and the detector. Consequently, since it becomes harder to control the amount of X-ray radiation, the deficiency of density continuity appears in the continuous image. Thus, diagnosis becomes much harder.

In order to improve a diagnostic ability by using a continuous image, such variations of image density need to be abolished among the divisional plurality of X-ray images so that the pasted continuous image can be seen as smooth as possible in the whole range. In particular, when such density variations are extremely large among divisional X-ray images, it becomes very important to make each of image displayed densities uniform by manually controlling gradations for each of the images. However, such a manual control of gradation, i.e., density, is extremely burdensome and time consuming for a reader since divisional lower legs angiography requires a lot of divisional X-ray imaging operations. Thus, the deficiency of the conventional methods worsens throughput of the inspection.

SUMMARY OF THE INVENTION

Accordingly, the present invention intends to solve the above-mentioned problems and defects for generating a continuous X-ray image by pasting together a plurality of successive divisional X-ray images. The present invention reduces burdensome operations for adjusting density variations among the plurality of divisional X-ray images and improves the throughput of the X-ray image inspection. The present invention provides an apparatus and method for processing X-ray images by adjusting and reducing density variations among the plurality of divisional X-ray images in order to generate a continuous X-ray image of a relatively uniform density.

According to one embodiment of the present invention, there is provided an X-ray image processing apparatus with an X-ray imaging device for obtaining a plurality of consecutive divisional X-ray images along an examined body, each of the divisional X-ray images including overlapped edge portions between two adjoining X-ray images along a consecutive direction of the divisional X-ray images in order to use an image gradation uniforming process. The apparatus includes a memory for storing X-ray image data of the plurality of consecutive divisional X-ray images; an ROI setting unit for setting up a region of interest (ROI) surrounding the substantially same inspection areas in each of the overlapped edge portions of image data for the adjoining X-ray images read out from the memory; an index value calculator for calculating an index value for the image data of the adjoining X-ray images based on a plurality of pixel values in the set-up ROI; a gradation calculator for determining or calculating a display gradation for the image data of the adjoining X-ray images corresponding to the index value; a gradation processing unit for altering or converting the pixel values for the plurality of X-ray image data so that the calculated display gradation for the image data of the adjoining X-ray may substantially coincide; and a continuous pasting operation unit for generating a continuous image of relatively uniform gradations by pasting together the plurality of X-ray image data of the converted display gradations.

According to another embodiment of the present invention, there is provided an X-ray image processing apparatus including a memory for storing the plurality of X-ray image data and a setting unit for setting up a measuring region of interest (ROI) for a pixel value profile. The ROI vertically crosses all the image data of the plurality of divisional X-ray images. The apparatus also has a profile forming unit for providing a pixel value profile in the set-up measuring ROI; a gradation processing unit for successively converting each display gradation for the plurality of divisional X-ray images. This gradation conversion continuously couples a display gradation corresponding to the pixel value profile for a reference image in the plurality of divisional images to a display gradation corresponding to a pixel value profile for an image adjoining the reference image. A continuous image processing unit generates a continuous image by pasting the plurality of divisional X-ray images of the converted display gradation.

In another embodiment of the present invention, there is provided an X-ray image processing apparatus having a gradation processing unit that successively performs conversions of the display gradations. The display gradation corresponds to an index value for the adjoining images calculated by the gradation calculator and is substantially uniform or uniform to the display gradation corresponding to another index value for a reference image calculated by the gradation calculator.

According to another embodiment of the present invention, there is provided a method for processing X-ray images. X-ray image data of the plurality of consecutive divisional X-ray images are stored in a memory. A region of interest (ROI) surrounding the same or substantially same inspection areas in each of the overlapped edge portions of image data for the adjoining X-ray images read out from the memory are set. An index value for the image data of the adjoining X-ray images is generated based on a plurality of pixel values in the set-up ROI. A display gradation for the image data of the adjoining X-ray images is calculated to correspond to this index value. The pixel values for the plurality of X-ray image data are converted so that the calculated display gradations for the image data of the adjoining X-ray images may coincide or substantially coincide. A continuous image of relatively uniform gradations is generated by pasting together the plurality of X-ray image data of the converted display gradations.

According to another embodiment of the present invention, there is provided a method for processing X-ray images that includes storing a plurality of X-ray image data in a memory, and setting up a measuring ROI for a pixel value profile. The ROI vertically crosses all the image data of the plurality of divisional X-ray images. A pixel value profile in the set-up measuring ROI is provided, and each of the display gradations for the plurality of divisional X-ray images is successively converted so as to continuously couple a display gradation corresponding to the pixel value profile for a reference image in the plurality of divisional images to a display gradation corresponding to a pixel value profile for an adjoining image to the reference image. A continuous image is generated by pasting together the plurality of divisional X-ray images of the converted display gradation.

BRIEF DESCRIPTION OF THE DRAWINGS

The accompanying drawings, which are incorporated in and constitute part of this specification, illustrate various embodiments and/or features of the invention and together with the description, serve to explain the invention. Wherever possible, the same reference numbers will be used throughout the drawings to refer to the same or like parts.

DETAILED DESCRIPTION OF THE PREFERRED EMBODIMENTS

Reference will now be made in detail to the exemplary embodiments of the present invention, examples of which are illustrated in the accompanying drawings. In general, an X-ray image processing apparatus can be applicable in an industrial use and a medical use. Since the basic features of the X-ray image processing apparatus in each of the industrial and medical applications are substantially the same, the apparatus and method for processing X-ray images according to the present invention may be applicable in both industrial use and medical use. For convenience of explanation, the following discussion relates to an X-ray image processing apparatus for the medical use, and in particular, to a digital X-ray image inspection apparatus.

Figure 1:
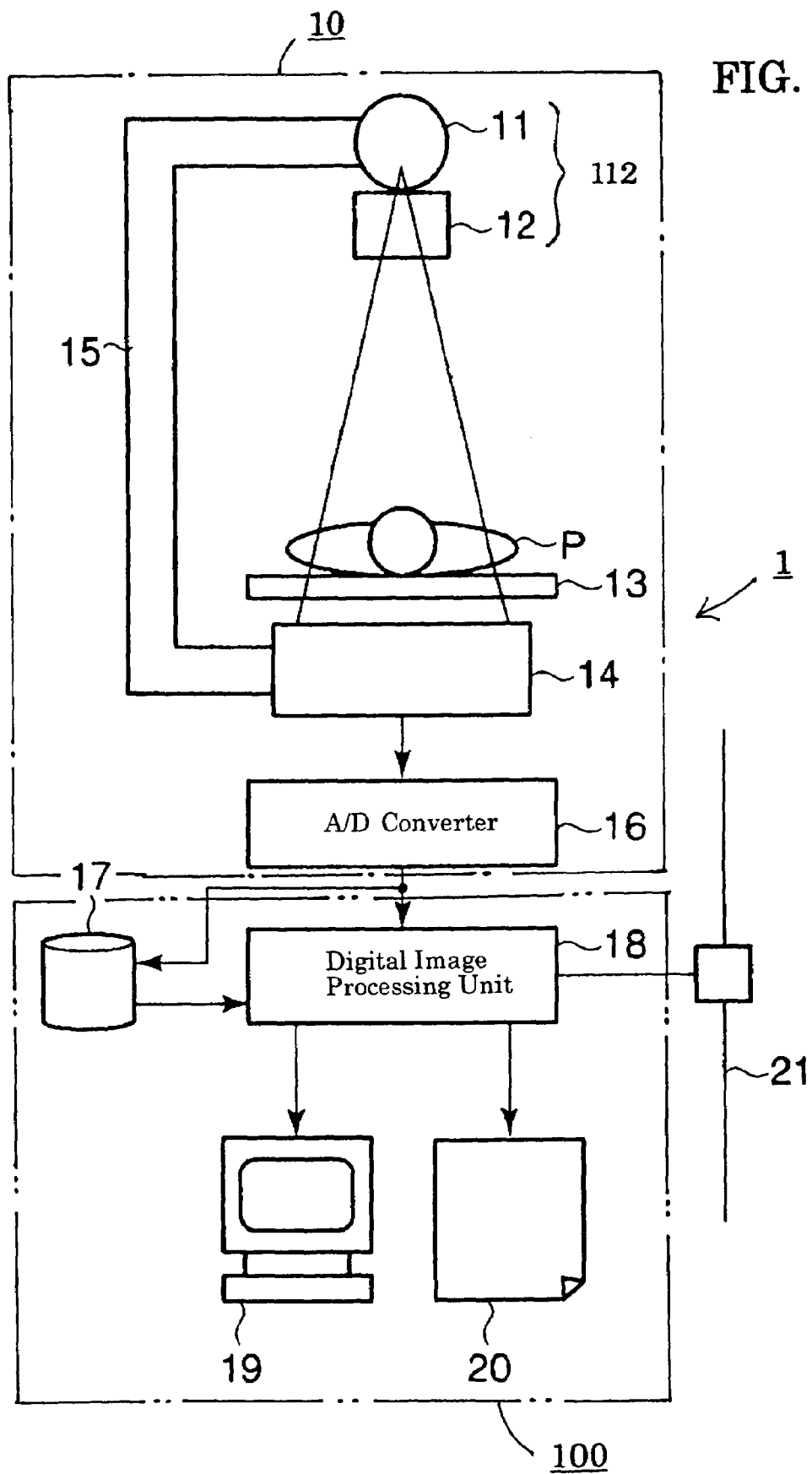
FIG. 1 is a block diagram of a digital X-ray inspection apparatus as an embodiment of the X-ray image processing apparatus of the present invention.

FIG. 1 illustrates a digital X-ray image inspection apparatus 1 of an embodiment of the invention. The digital X-ray image inspection apparatus 1 is comprised of an X-ray image detection apparatus 10 for obtaining X-ray images and a digital image processing apparatus 100 for processing the obtained X-ray images. The X-ray image detection apparatus 10 includes an X-ray tube 11 and an X-ray diaphragm 12 provided on a radiation window of the X-ray tube for limiting the X-ray radiation field. The X-ray tube 11 and the X-ray diaphragm 12 constitute an X-ray source 112. The X-ray image detection apparatus 10 further includes an X-ray detector 14 for detecting X-rays penetrated through a patient P laid on a top plate 13 of a bed.

An X-ray source 112 and an X-ray detector 14 are respectively mounted on each edge of a U-shaped interlocked frame 15 so as to move from head to toe of a patient (an examining body) P laid on a top plate 13. There are two main types of X-ray detector 14. One is constructed by combining an image intensifier (I.I.) and a camera. The other is constructed as a plain detector. The former type of detector converts the penetrated X-rays into visible light through the I.I., and the visible light is converted into electric data through the camera. On the other hand, the plain detector directly converts the penetrated X-ray into electric data through the detection elements. In either case, the incident X-ray image data on the X-ray detector are supplied to a digital image processing apparatus 100 as electric data.

Figure 2:
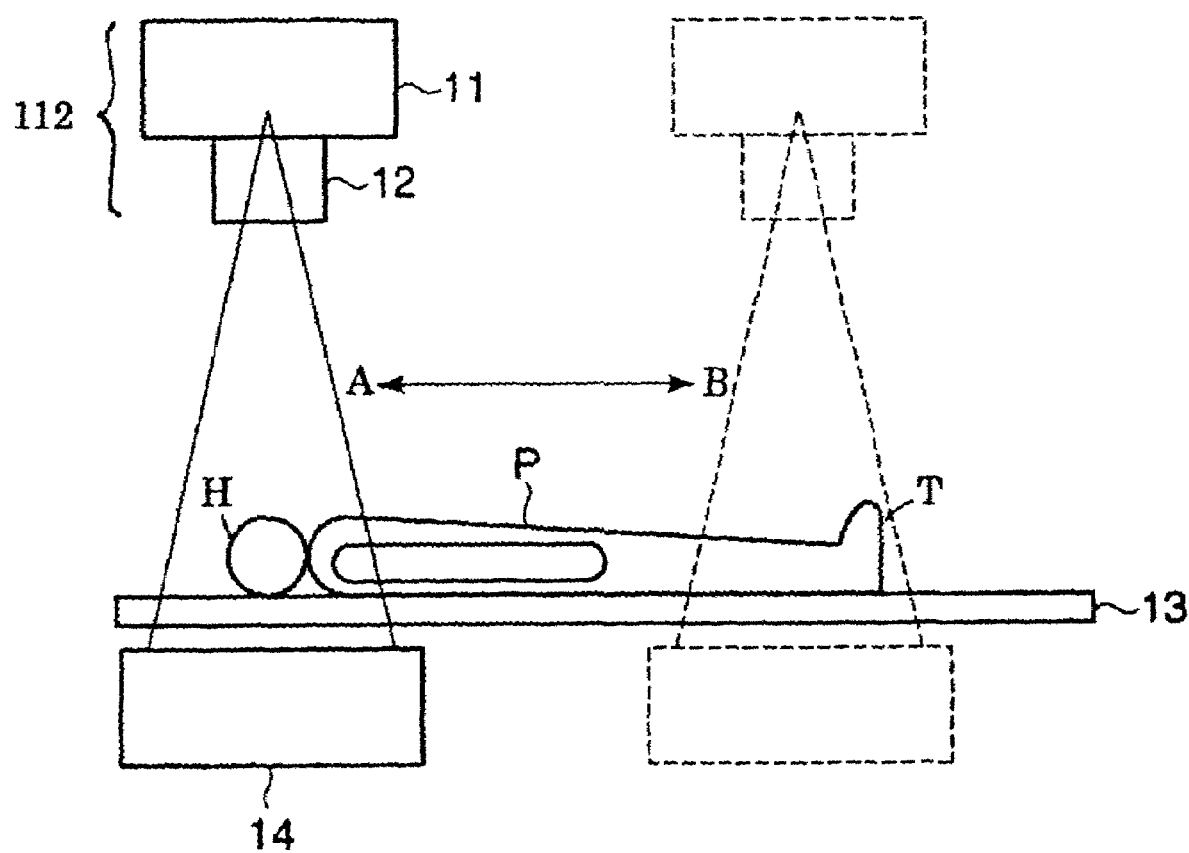
FIG. 2 is a schematic illustration for explaining how to obtain a plurality of consecutive divisional X-ray images without moving an examining body, e.g., a patient, according to one embodiment of the invention.

The interlocked frame 15 is movably mounted on a ceiling, a floor, or rails provided on the ceiling (not shown). By moving the interlocked frame 15, it becomes possible to obtain a plurality of X-ray images without moving an examining body, e.g., a patient P. As shown by an arrow A-B in FIG. 2, by moving an interlocked pair of X-ray source 112 and detector 14 along a body axis (a long axis) of a patient P on a top plate 13, it becomes possible to obtain a plurality of X-ray images covering a wide range from a head top H to toes T of the patient P.

Figure 3:
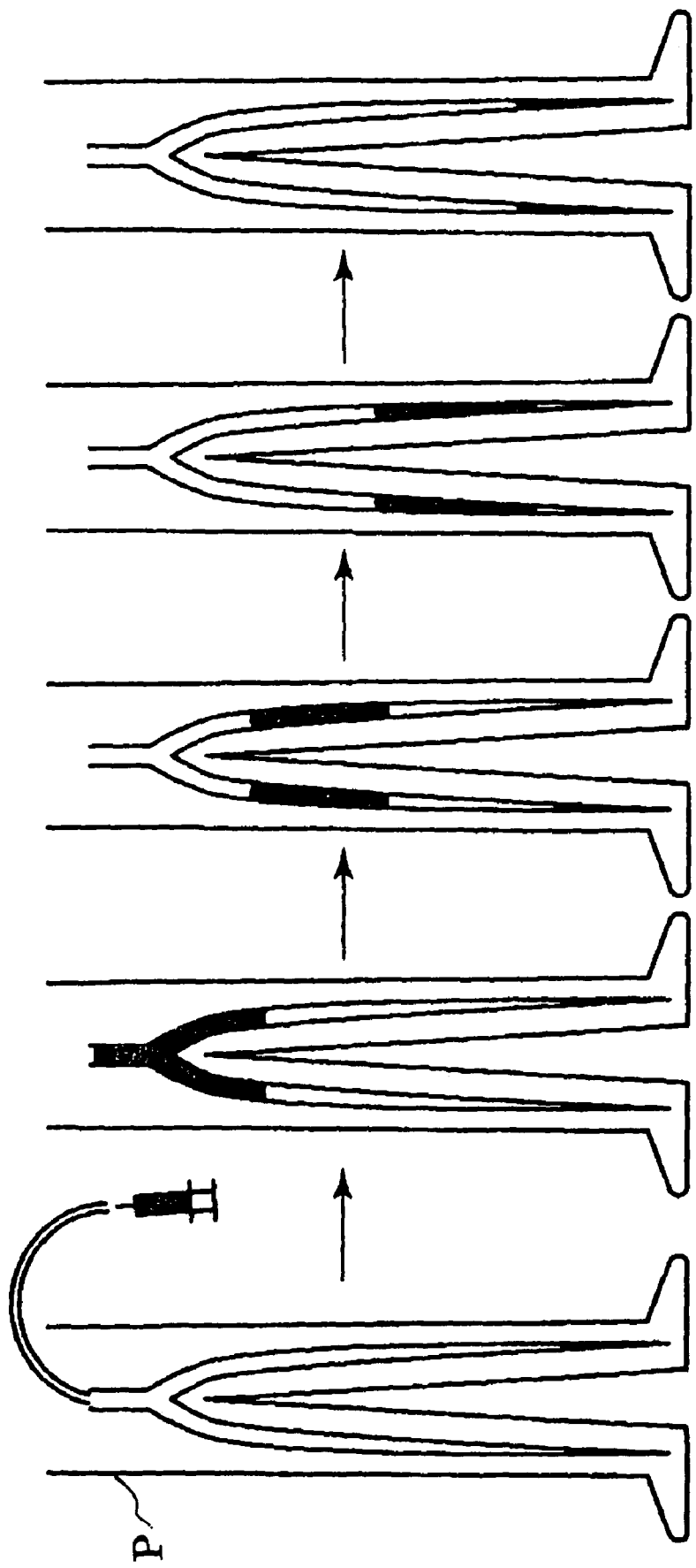
FIGS. 3A-3E are schematic illustrations for explaining how to obtain a plurality of consecutive divisional X-ray images for a digital X-ray inspection apparatus.

FIGS. 3A-3E explains a flow of an injected contrast agent in lower legs angiography as an example of inspection utilizing a plurality of X-ray images. As illustrated in FIG. 3A, a contrast agent is injected into the artery of a patient P's abdomen through a catheter. The contrast agent riding on the blood flow travels from the abdomen (FIG. 3B) to a toe portion (FIG. 3E) passing through a thigh portion (FIG. 3C) and a knee portion (FIG. 3D). By successively repeating X-ray imaging with pursuing the flow of the contrast agent, it becomes possible to obtain a consecutive plurality of X-ray images along a body axis of a patient P. In the lower legs angiography according to the present invention, the plurality of consecutive X-ray images are obtained so that each edge portion of the adjoining images are slightly overlapped for utilizing a pasting process.

Figure 4:
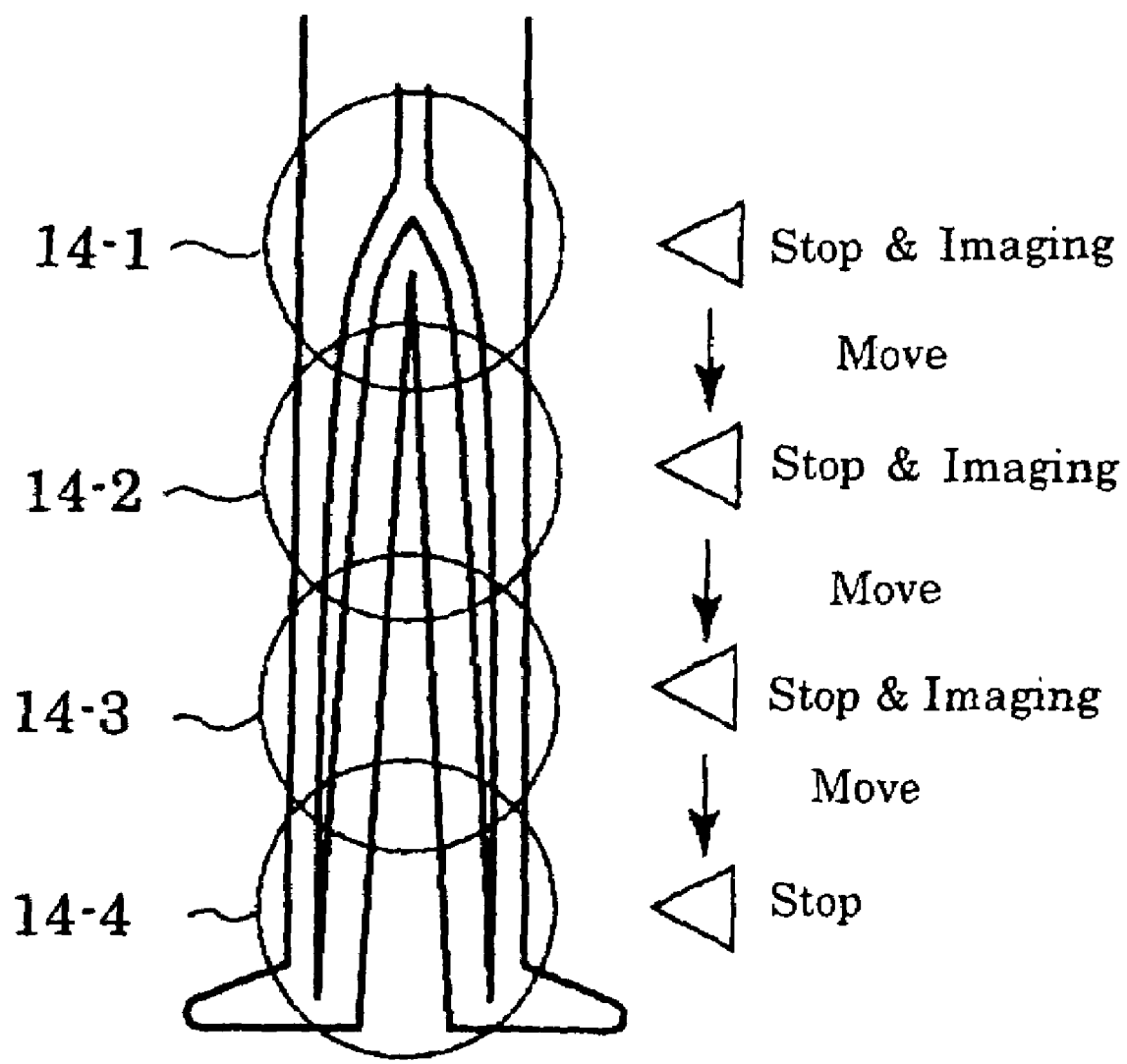
FIG. 4 is a schematic illustration for explaining a stepping method for obtaining a plurality of consecutive divisional X-ray images for the lower legs angiography.

To obtain the plurality of consecutive X-ray images for utilizing the lower legs angiography, there are two methods. One is a stepping method and the other is a bolus chase method. FIG. 4 explains the operations for obtaining a plurality of consecutive X-ray images by the stepping method. In FIG. 4, the circles 14-1 to 14-4 respectively indicate an X-ray detection area in which the detector 14 in FIG. 1 detects the X-ray radiated from the X-ray source 112 and penetrated through the patient's lower legs. When the pair of the X-ray source 112 and detector 14 completes imaging at a detection position 14-1, i.e., a contrast agent arrival position as illustrated in FIG. 3B, the pair of the X-ray source 112 and detector 14 is quickly moved to a next imaging position 14-2, i.e., a contrast agent arrival position as illustrated in FIG. 3C, earlier than the flow of the contrast agent in the blood vessel of the lower legs. Until arrival of the contrast agent, the pair pauses. Upon the arrival of the contrast agent, the pair executes an imaging operation at the position 14-2. Again, the pair moves quickly to a next imaging position 14-3, i.e., a contrast agent arrival position as illustrated in FIG. 3D. By repeating these intermittent operations of X-ray imaging, moving, pause, and X-ray imaging, the apparatus 10 can obtain a plurality of consecutive X-ray images with a wide range from an imaging start position 14-1 to an imaging finish position 14-4 covering the whole of the lower legs.

Figure 5:
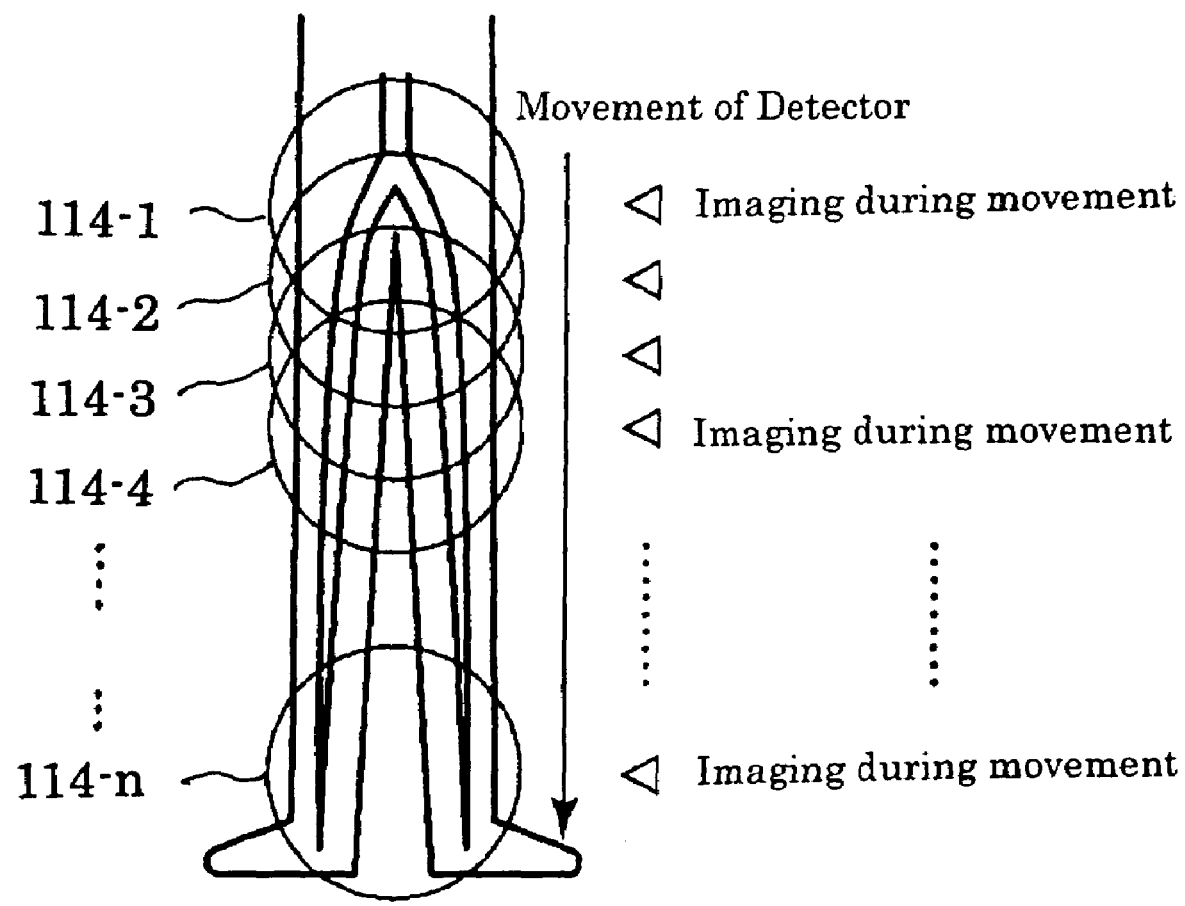
FIG. 5 is a schematic illustration for explaining a bolus chase method for obtaining a plurality of consecutive divisional X-ray images for lower legs angiography.

FIG. 5 explains the bolus chase method for obtaining a plurality of consecutive X-ray images. Similar to FIG. 4, each of the circles 114-1 to 114-n indicates an X-ray detection area detected through the detector 14. In the bolus chase method, the pair of the X-ray source 112 and detector 14 repeats an X-ray imaging operation while pursuing or following of the flow of the contrast agent. Thus, during the movement of the pair of X-ray source 112 and detector 14 along the body axis of the patient, as shown by the arrow in FIG. 5, X-ray images are successively obtained at each of the imaging positions 114-1 through 114-n in a short time.

Figure 6:
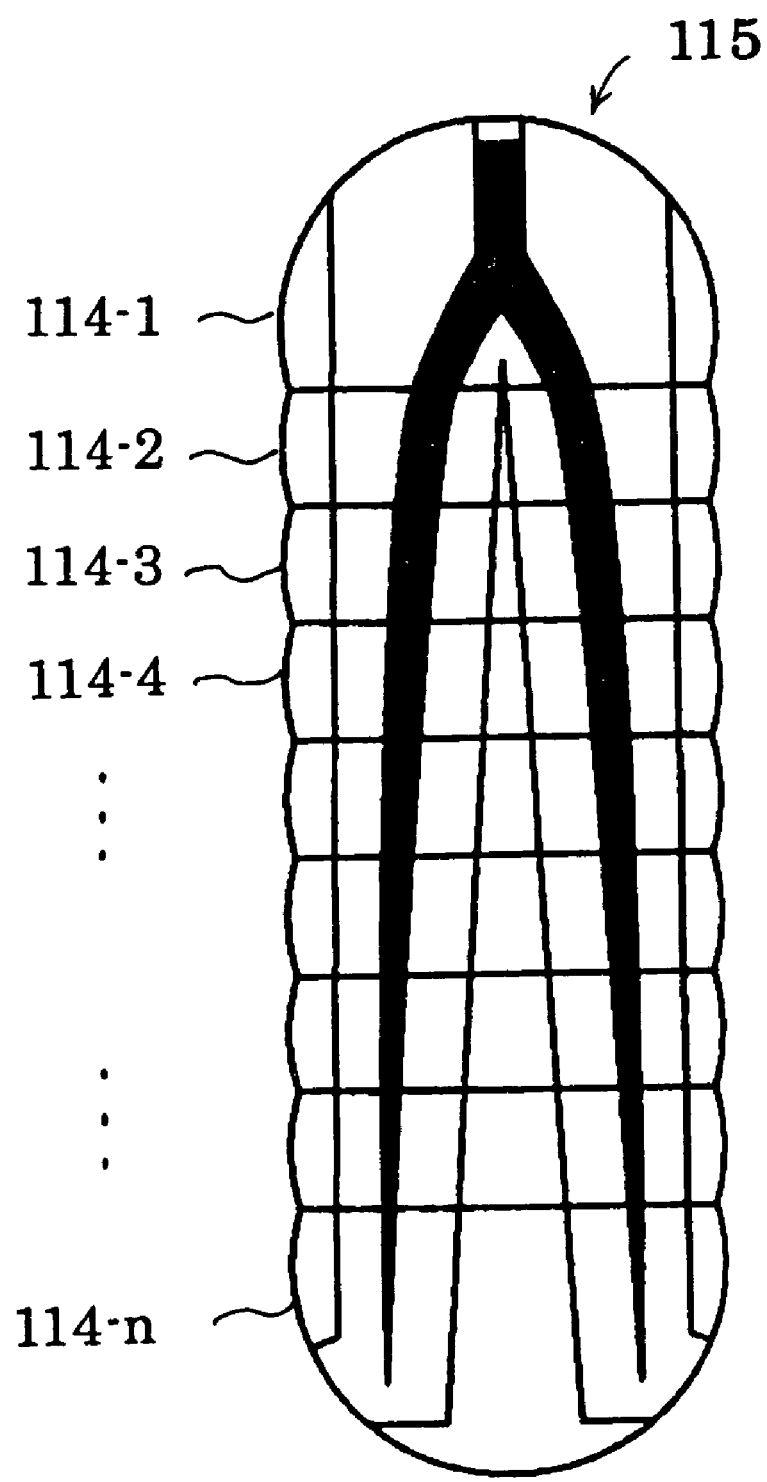
FIG. 6 is a schematic illustration for explaining an example of a continuous image, for use in lower legs angiography, that is generated by pasting the plurality of consecutive divisional X-ray images obtained by the stepping method or the bolus chase method.

The plurality of consecutive X-ray images are pasted along their edge portions for the lower legs angiography, as illustrated in FIG. 6. Thus, a continuous image 115 is generated and displayed by pasting the plurality of divisional X-ray images ranging from the abdomen 114-1 to the toe portion 114-n for the inspection.

Turning back to FIG. 1, the X-ray image processing device 100 includes an analog/digital (A/D) converter 16 for converting the penetrated X-ray information supplied from the detector 14 into digital image data; a storing apparatus 17, such as an optical disk apparatus for storing digital image data; a digital image processing unit 18 for performing various processing of digital image data, such as an edge highlighting process, a gradation process, and a pasting process for generating a continuous image from a plurality of divisional images; a monitor 19 for displaying the pasted continuous image; and a film imager 20 for printing the pasted continuous image. It is also possible to store the processed image data in the digital image processing device 18 in the storing apparatus 17, or to transfer the processed image data to external equipment through a network 21.

Figure 7:
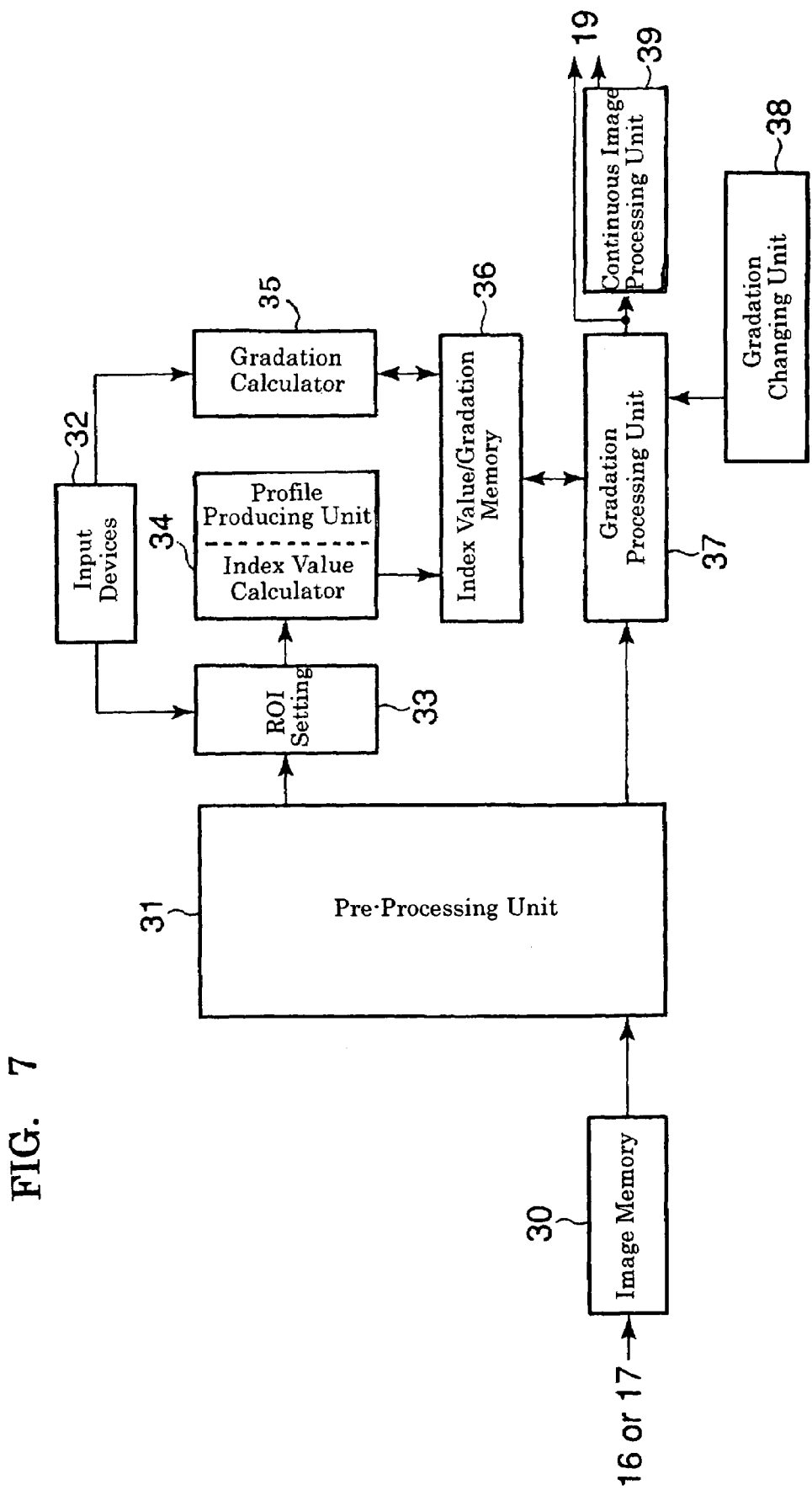
FIG. 7 is a block diagram of an embodiment of a digital image processing apparatus for generating a continuous X-ray image in the X-ray image processing apparatus of the present invention.

FIG. 7 illustrates an exemplary structure of the digital image processing device 18 in FIG. 1. The digital image processing device 18 includes an image memory 30, a pre-processing unit 31, input/output equipment 32, a region of interest (ROI) setting unit 33, an index value calculator 34, a gradation calculator 35, an index value/gradation memory 36, a gradation processing unit 37, and a continuous image processing unit 39. Image memory 30 temporarily stores a plurality of consecutive X-ray images supplied from the A/D converter 16 or the storing apparatus 17 shown in FIG. 1. The pre-processing unit 31 performs pre-processing, such as digital compression for compressing pixel values higher or lower for portions of the background in the X-ray image data read out from the image memory 30 in order to increase image sharpness without losing necessary information, a compensation filtering process, a space filtering process or any other desirable processing. The gradation processing unit 37 converts the pre-processed pixel values for the plurality of X-ray images into linearly display gradations or non-linearly display gradations. In general, there are two kinds of gradation processes. One is a linear display gradation process that is called a window process, and the other is a non-linear display gradation conversion process (gamma process) corresponding to a curved gamma correcting function. Further, it is also possible to perform the conversion by combining the gamma process and the window process. To simplify the explanation, the following embodiments of the invention use the gamma process only.

Figure 8:
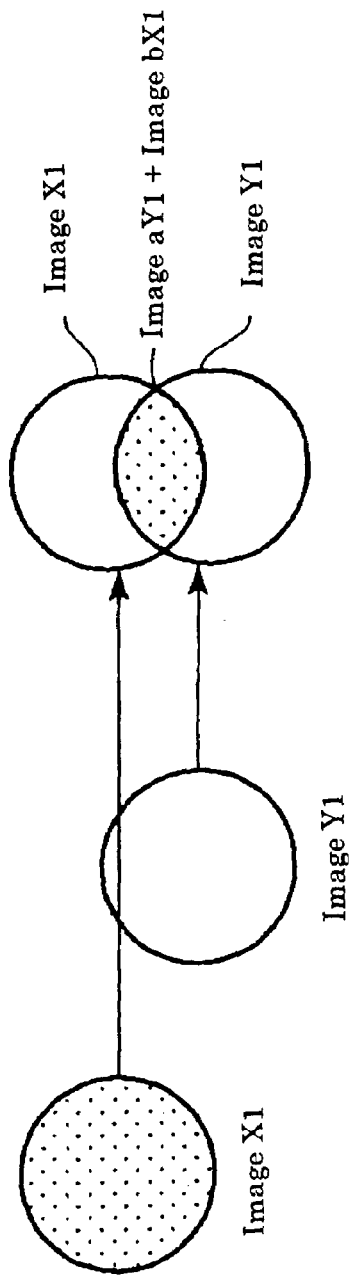
FIG. 8 is a schematic illustration for explaining how two adjoining divisional images are pasted by weighting them in order to use partially overlapped portions between them.
Figure 9:
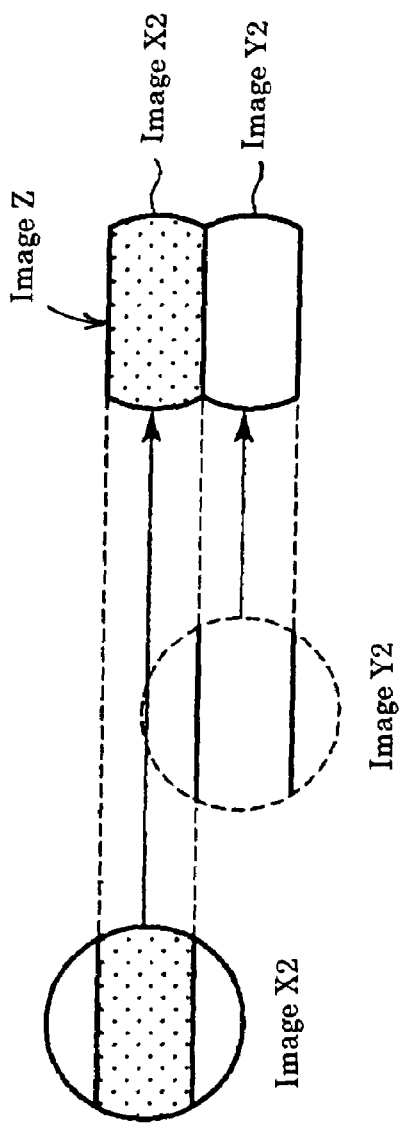
FIG. 9 is a schematic illustration for explaining how two adjoining divisional images are pasted.

The continuous image processing unit 39 generates a continuous image by pasting the plurality of X-ray images of a respectively processed gradation. In the continuous image processing unit 39, two kinds of algorithms are installed in order to paste the plurality of images. FIG. 8 explains a principle for the first pasting algorithm. Thus, this method composes the converted consecutive X-ray images X1 and Y1 in the gradation processing unit 37 at the overlapped portion. Thus, the overlapped portion is obtained by weighting X1 and Y1 by factors b and a, respectively. FIG. 9 explains a principle for the second pasting algorithm. This method generates a continuous image Z by trimming the gradation converted consecutive X-ray images X2 and Y2 at the respective pasting boundary line before pasting. In one embodiment, an operator can select either of the first or second pasting algorithm in the continuous image processing unit 39.

As shown in FIG. 7, the digital image processing apparatus of the present invention further includes region of interest (ROI) setting unit 33, an index value calculator 34, a gradation calculator 35, an index value/gradation memory 36, and a gradation processing unit 37 for relatively uniform processing gradation to reduce variations of the display gradations among the plurality of images before performing the pasting operation in the continuous image processing unit 39.

Figure 10:
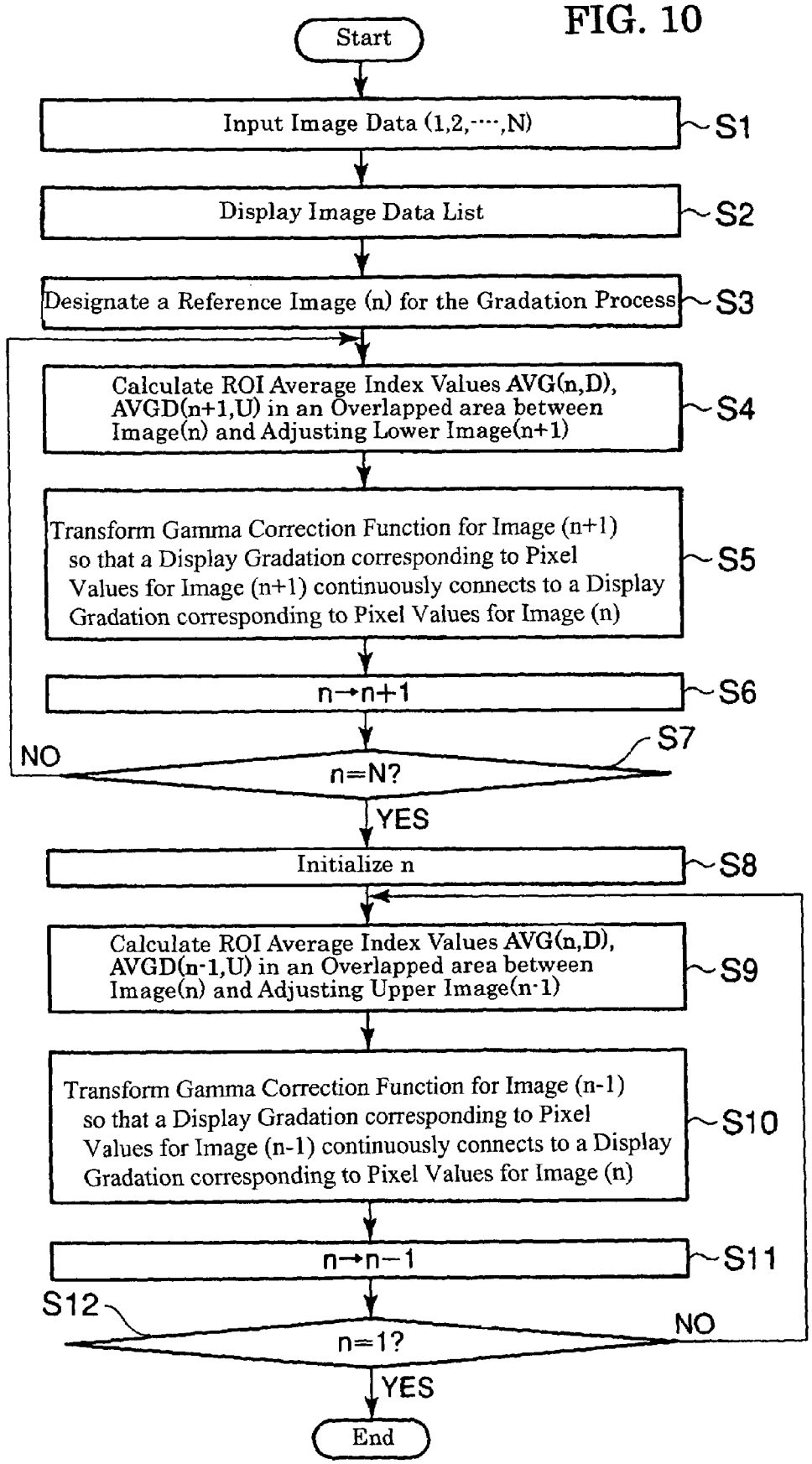
FIG. 10 is a flowchart illustrating a pasting process for generating a continuous image in a digital image processing apparatus according to one embodiment of the present invention.
Figure 11:
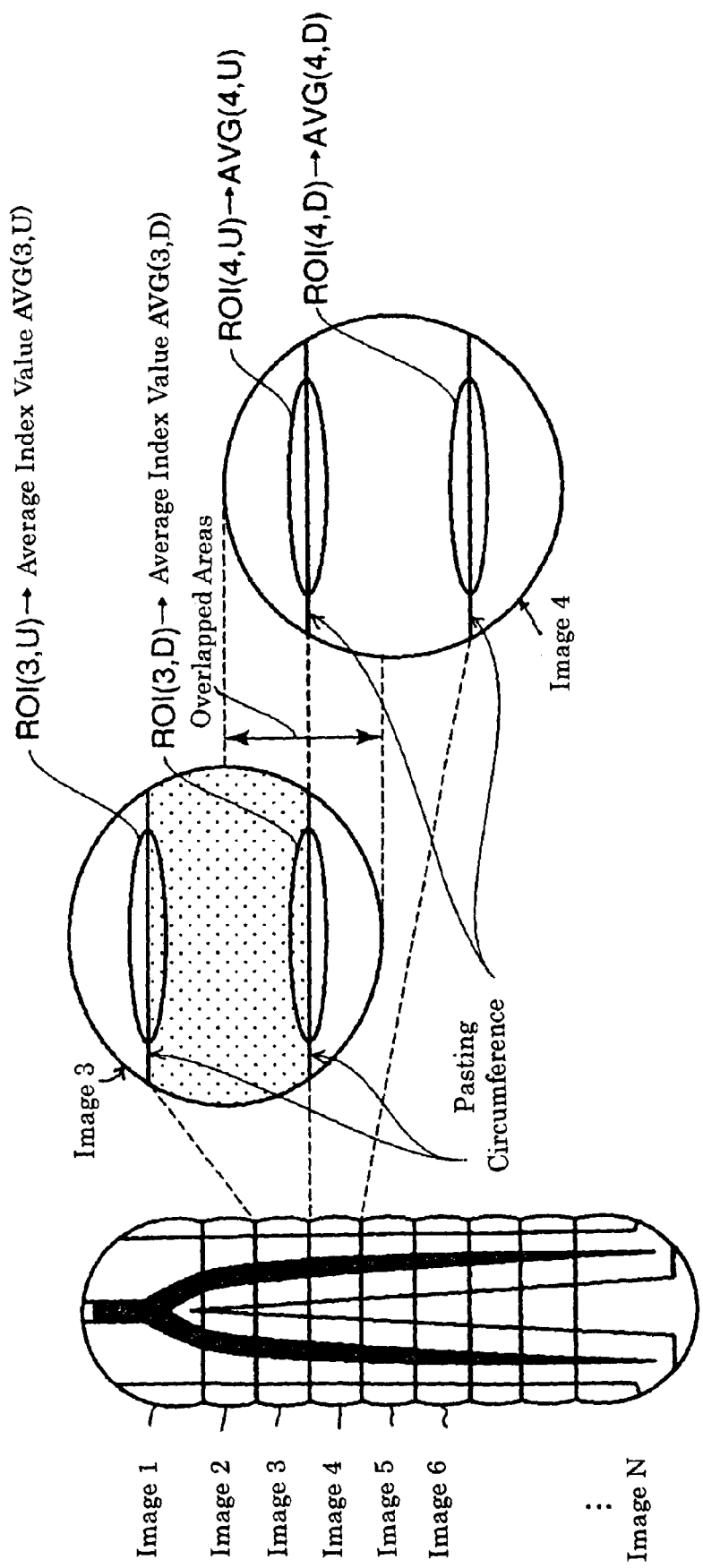
FIG. 11 is a schematic illustration for explaining a pixel average value calculating method in each of regions of interest (ROI) for an overlapped portion between two adjoining consecutive images for use at Step S4 in FIG. 10.

FIG. 10 is a flowchart for illustrating an embodiment of the continuous image gradation uniforming process utilized in the X-ray image processing apparatus consistent with the present invention. At first, a plurality of consecutive X-ray image data 1,2 . . . , N is input from the A/D converter 16 or the storing apparatus 17 to the image memory 30 in the digital image processing unit 18 (Step S1). As illustrated in FIG. 11, each of the plurality of X-ray image data is respectively allotted an identification (ID) number, image 1, . . . , image N in the input order, in order to generate a continuous image by pasting the consecutive X-ray images in order.

The plurality of consecutive X-ray image data 1, . . . , N is processed in the pre-processing unit 31, and an initial gradation process is performed in the gradation processing unit 37 in order to display an image data list on the monitor 19 (Step S2). It is also possible to display a continuous image after pasting the plurality of images in the continuous pasting unit 39, since the input/output relation for the plurality of consecutive X-ray images is initially matched for the gradation process. An operator designates a particular X-ray image (n) as a reference image for the gradation uniformity process among the displayed list for the plurality of consecutive X-ray images on the monitor 19 (Step S3). For example, when it is judged that the image 3 has the most appropriate display gradation for the lower legs angiography among the displayed list in FIG. 11, an operator designates the image 3 as the reference image by using input equipment 32, such as a keyboard or a pointing device. It is also possible to slightly adjust the display gradation of the reference image by operating a gradation changing unit 38, depending on preference. In accordance with this adjustment, the input/output relation for the initial gradation process for the images is determined.

When the reference image is designated, a region of interest (ROI) that surrounds the same or substantially the same inspecting portions in each of the overlapped portions between the reference image and an X-ray image adjoining the reference image is set up through the input equipment 32. As illustrated in FIG. 11, for instance, an ROI (3, U) is set up at an upper edge side of the reference image 3 in the overlapped portion between an upper adjoining image 2, and an ROI (3, D) is set up at a lower edge side of the reference image 3 in the overlapped portion between a lower adjoining image 4. Similarly, on the image 4, an ROI (4, U) is set up at an upper edge side of the image 4 in the overlapped portion between an upper adjoining reference image 3, and an ROI (4, D) is set up at a lower edge side of the image 4 in the overlapped portion between a lower adjoining image 5. As a matter of course, the ROI (3, D) and the ROI (4, U) are set up at the same portion.

Similarly, in consecutive order, each ROI is set up at the upper and lower edge portions for the respective images 1 to N.

The ROI is set, for example, by automatically setting up in an overlapped portion, a parameter presetting method in which an operator preliminarily decides a position, a shape, and a size for the ROI, or by an operator directly inputting the respective ROI by using the pointing device. It is also possible to set up a plurality of ROIs in the same portions in each of the overlapped portions. For lower legs angiography, the ROI is respectively set up on each of a right and a left leg. With the present invention, any of the above methods or other suitable methods is applicable.

When an ROI is set up, ROI setting unit 33 reads a plurality of pixel values in the set up ROI from the pre-processing unit 31 and supplies them to an index value calculator 34. The index value calculator 34 calculates an index value based on the plurality of pixel values in the ROI and stores them in an index value/gradation memory 36. As the index value, each of an average value, a maximum value, a minimum value, a center value, and/or the most frequent value for the plurality of pixel values in an ROI is obtained by a calculation. In this particular embodiment of the invention an index value and an average value are obtained.

In order to obtain the average value, several methods can be applicable. A first method is to obtain an average value for whole pixels in the ROI. A second method is to obtain an average value in a predetermined numerical value range. A third method is to obtain an average value by using an average value in a set up order range when the order range is predetermined by arranging the pixel values in a smaller value. A fourth method is to obtain an average value of pixels from a valley or peak to another valley or peak in a histogram of all pixels in the ROI. Of course, it is possible to combine some of these methods. The average value obtaining method is determined so as to avoid error factors caused by an X-ray diaphragm or directly detected X-rays between the legs in the lower legs angiography, or position slippage of a subtraction image.

Turning to FIG. 10, as explained above, an average pixel value AVG (n, D) for a lower edge side ROI of the reference image n and an average pixel value AVG (n+1, U) for an ROI in an overlapped portion between the reference image n and a lower edge side of an adjoining image (n+1) are calculated (Step S4). In this embodiment consistent with the invention, the index value calculator 34 calculates an average pixel value AVG (3, D) for a lower edge side ROI of the reference image 3 and an average pixel value AVG (4, U) for an upper side ROI of lower side image 4 adjoining to the reference image 3.

Figure 15:
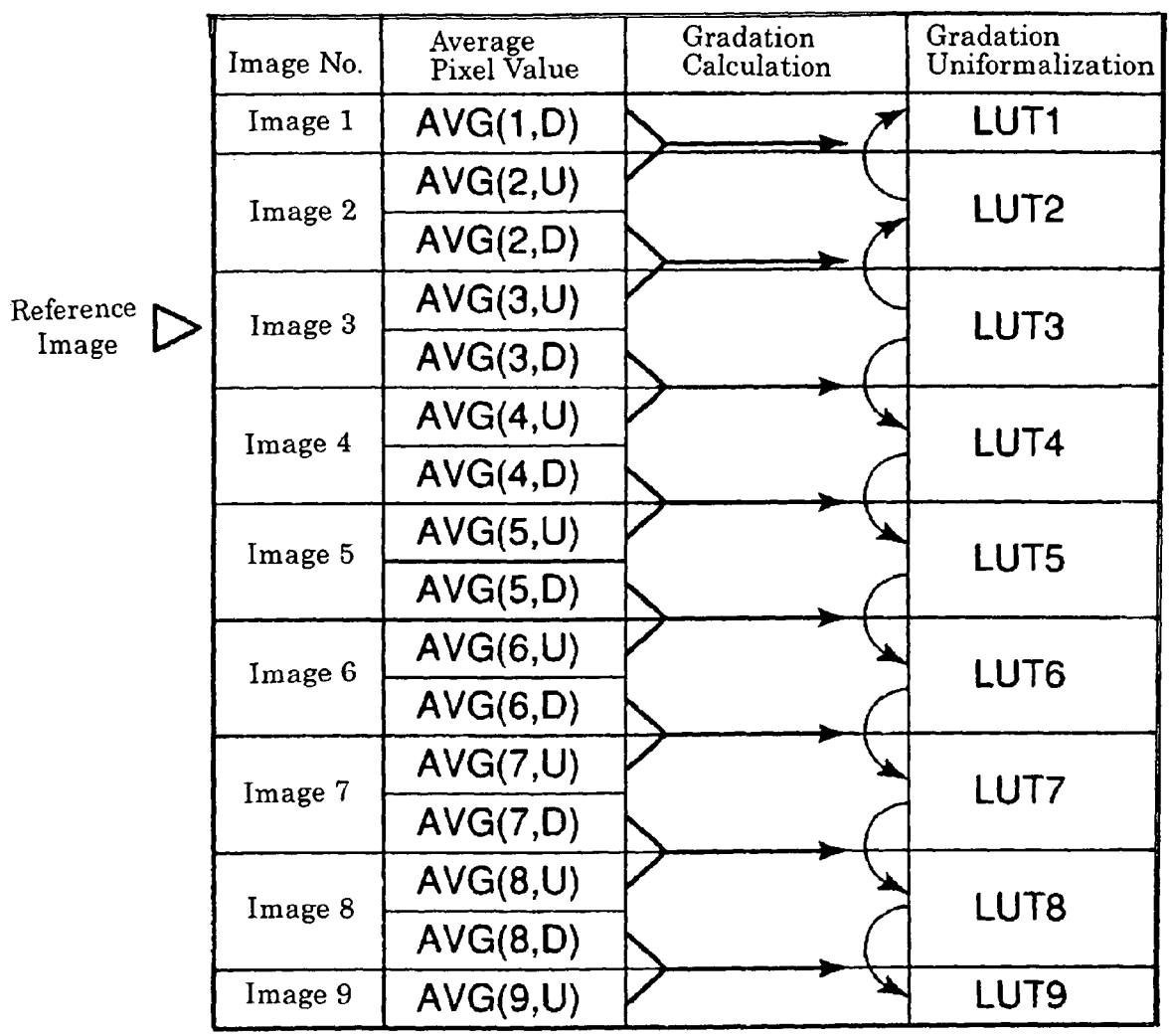
FIG. 15 is a chart for conceptually explaining an embodiment of the gradation adjusting process for making the plurality of consecutive divisional images relatively uniform, based on each gradation calculation of the respective average pixel value.

The index values stored in the index value/gradation memory 36, i.e., average values in the embodiment consistent with the invention, are read by the gradation processing unit 37 in order to use in a gradation uniformity process. As illustrated in FIG. 15, starting from the point of the reference image 3, the gradation uniforming process compensates the input/output relations of the gradation process so as to become equal to the display gradation LUT3 corresponding to the index value AVG (3,U) for the reference image 3 to the display gradation LUT2 corresponding to the index value AVG (2,D) for the upper side image 2 adjoining the reference image 3. Further, the gradation uniformity process compensates the input/output relations of the gradation process so as to become equal to the display gradation LUT3 corresponding to the index value AVG (3,U) for the reference image 3 to the display gradation LUT4 corresponding to the index value AVG (4,U) for the lower side image 4 adjoining the reference image 3. Similarly, the input/output relations for the gradation processes are successively compensated so as to become equal to the display gradation corresponding to the index value for an upper screen and a lower adjoining screen. In this embodiment of the invention, the input/output relation of gradation process is provided by a gamma correcting function. Thus, the same gamma correcting function for all of the plurality of X-ray images 1, . . . , N is set up at an initial stage. The reference image 3 is fixed by the initial gamma correcting function. The gamma correcting functions for other images are compensated so that each of the display gradations in the same ROI becomes equal to the reference image 3.

In FIG. 10, the gradation calculator 35 corrects or adjusts a display gradation Dn corresponding to average pixel value AVG (n, D) for a lower edge side ROI of the reference image n in accordance with a gamma correcting function, and further performs a correction of a display gradation Dn+1 corresponding to an average pixel value AVG (n+1, U) for an upper edge side ROI of an image n+1 in accordance with the same gamma correcting function. Then, the gamma correcting function is transformed so as to coincide with the display gradation Dn+1 after performing the gamma correction to the display gradation Dn after performing the gamma correction (Step S5).

Figure 12:
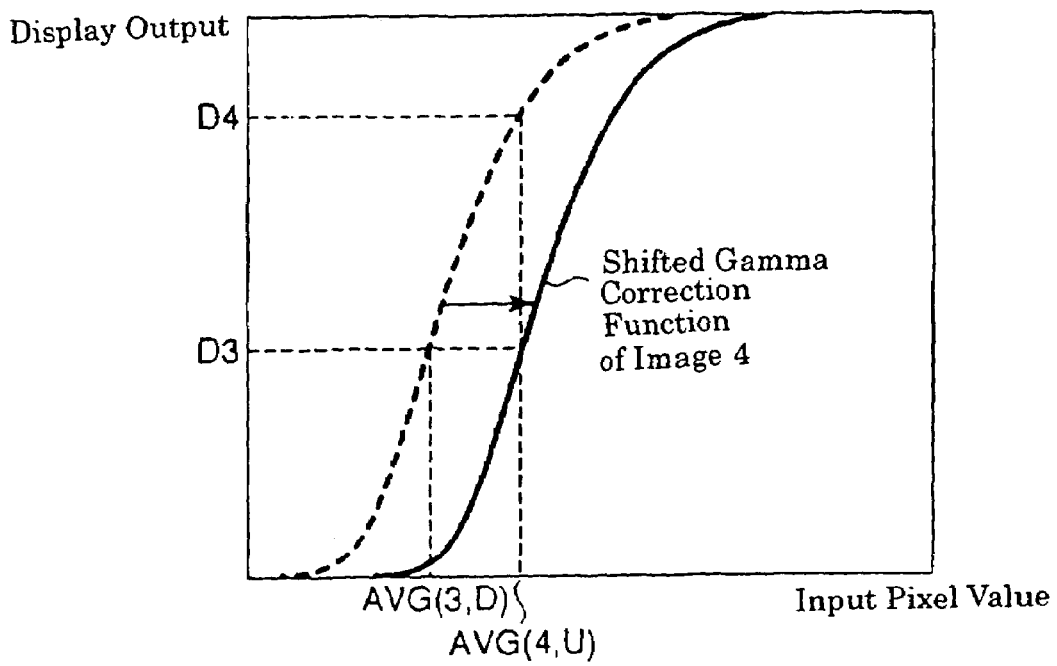
FIG. 12 is a graph for explaining an embodiment of the invention for transforming a gamma function so as to match the display gradation of an adjoining image based on the calculated pixel average value for use at Step S5 in FIG. 10.

In this embodiment, a display gradation D3 corresponding to an average pixel value AVG (3,D) for a lower edge side ROI of the reference image 3 is corrected in accordance with an initial gamma correcting function in the index value/gradation memory 36. Further, the display gradation D4 corresponding to an average pixel value AVG (4, U) for an upper edge side ROI of the image 4 is corrected in accordance with the same initial gamma correcting function. As illustrated in FIG. 12, the displayed output D4 of the display gradation corresponding to average pixel value AVG (4, U) for an upper edge side ROI of the image 4 is corrected for the input/output relation, i.e., a gamma correcting function for the gradation process so that the displayed output D4 corresponding to an average pixel value AVG (3, D) for an upper edge side ROI of the image 4 is shifted to the displayed output D3 corresponding to a lower edge side ROI of the reference image 3. Conceptually, the gamma correcting function for image 4 is transformed in a parallel direction along the input axis according to the difference of the average pixel value AVG (4, U) and the average pixel value AVG (3, D).

Figure 13:
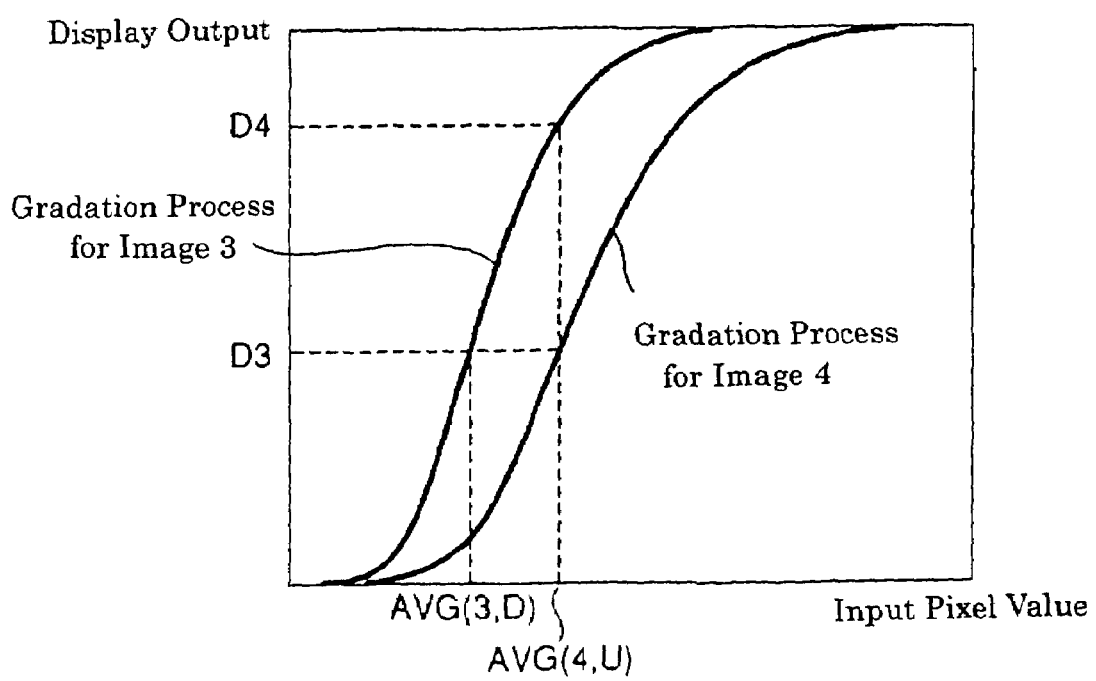
FIG. 13 is a graph for explaining another embodiment for adjusting a display gradation of an adjoining image.

In order to correct or adjust the input/output relation of the gradation process corresponding to the image 4, as illustrated in FIG. 13, it is also possible to produce the gamma correcting function for the image 4 by expanding the gamma correcting function for the reference image 3 in a direction of the input axis by a ratio of the average pixel value AVG (4, U) of an upper side ROI of the image 4 against the average pixel value AVG (3, D) for a lower edge side ROI of the reference image 3. Without performing the transformation of the gamma correcting function for the image 4, it is also possible to convert the input value, i.e., the pixel value for the image 4 in accordance with the difference or the ratio by fixing the input/output relation of the gradation process.

Practically, the method for transforming the gamma correcting function for the image 4 in a parallel direction along the input axis is suitable for pasting digital subtraction angiography (DSA) images. On the other hand, the pixel value conversion method in accordance with the difference or the ratio by fixing the input/out relation of the gradation process gradation is suitable for pasting digital angiography (un-subtraction DA) images.

Figure 14:
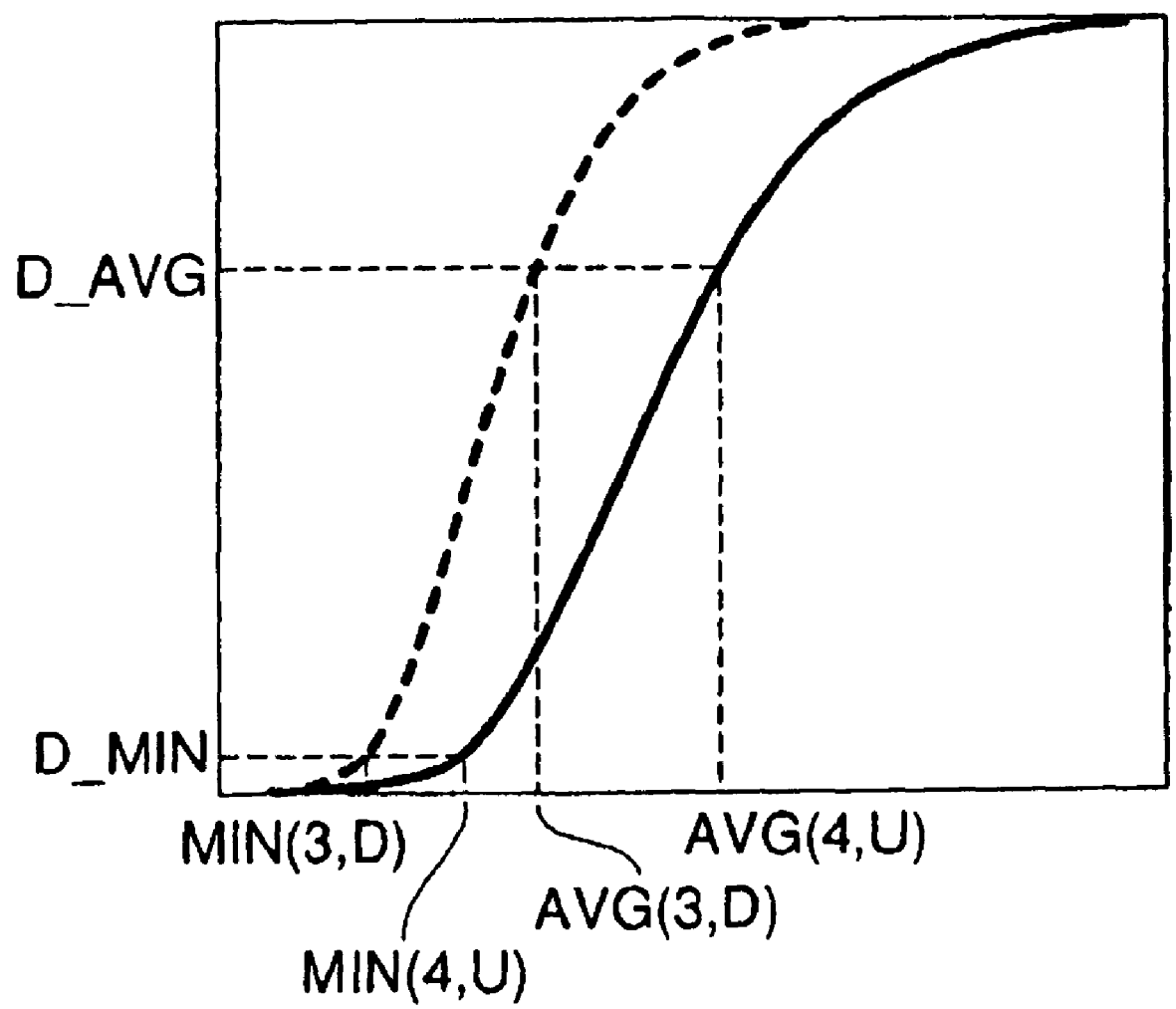
FIG. 14 is a graph for explaining another embodiment for transforming a gamma function as to match the display gradation of an adjoining image based on the calculated pixel average value for use at Step S5 in FIG. 10.

It is also possible to use two kinds of index values for performing the gradation correction. In this case, as illustrated in FIG. 14, the gamma correcting function for the image 4 is corrected so as that a displayed output gradation D_MIN for the minimum value MIN (3, D) obtained at the lower edge side ROI of the reference image 3 and a gradation D_AVG for average value AVG (3, D) obtained at the lower edge side ROI of the reference image 3 are corrected so as to respectively pass the minimum value MIN (4, U) and the average value AVG (4, U) obtained at the upper side edge ROI of the image 4. In accordance with the gradation correcting process, the gradation processing unit 37 converts all of the pixel values for the image 4 into the display gradation.

When the correcting operation for the pixel values of the image 4 into display gradations is complete, the image ID number n is incremented by 1 (Step S6, in FIG. 10). Then, it is judged whether the image ID number has reached the final image ID N for pasting (Step S7). If the image ID number has not reached the objective image ID number N (Step S7, NO), the process goes back to Steps S4 and S5 for performing gradation correction of image 5 based on the corrected image 4 as a reference. Thus, index value calculator 34 calculates average pixel value AVG (4, D) for a lower edge side ROI of image 4 and average pixel value AVG (5, U) for an upper edge side ROI of image 5 adjoining the reference image 4. Then, gradation calculator 35 specifies a display gradation corresponding to average pixel value AVG (4, D) of image 4 in accordance with the transformed gamma correcting function. The gradation calculator 35 further calculates a transforming amount of gamma correcting function for image 5 so as that display gradation corresponding to ROI average pixel value AVG (5, U) of image 5 may coincide to the display gradation corresponding to average pixel value AVG (4, D) of the reference image 4. Then, gradation processing unit 37 converts all of the pixel values for the image 5 to display gradation in accordance with the transformed gamma correcting function.

By doing this, the respective ROI display gradations for the images 4-N, consecutively arranged in a lower direction from the reference image 3 can be adjusted into a relatively uniform display gradation by successively correcting each display gradation.

When the display gradation adjusting process for adjusting the gradations of the plurality of images arranged at a lower side of the reference image into a relatively continuous gradation has completed, the reference image ID n is again initialized (Step S7). In this embodiment, the reference image ID n is initialized to 3, i.e., n=3. This time, each gradation correcting process for the respective images consecutively arranged to an upper edge side of the reference image 3 may be performed in order. Similar to Step S4, index value calculator 34 calculates pixel values AVG (n, U), AVG (n–1, D) for the respective overlapped portions between the upper edge side ROI of the reference image n and a lower edge side ROI of an image n–1 adjoining the upper edge side of the reference image n (Step S9). Thus, the average pixel value AVG (3, U) for the upper edge side ROI of the reference image 3 and the average pixel value AVG (2, D) for a lower side ROI of image 2 adjoining the upper edge side of the reference image 3 are respectively calculated. The calculator 35 corrects a display gradation corresponding to the average pixel value AVG (3, U) of the reference image 3 in accordance with the initial gamma correcting function in the memory 36, and corrects a display gradation corresponding to an average pixel value AVG (2, D) for ROI of image 2 in accordance with the same initial gamma correcting function.

Thus, the gradation calculator 35 transforms the gamma correcting function so as that the gamma corrected display gradation Dn–1 corresponding to average pixel value AVG (n–1, D) of a lower ROI for the upper side image n–1 coincides with the gamma corrected display gradation Dn corresponding to average pixel value AVG (n, U) of an upper ROI for the reference image n (Step S10).

Then, the image ID number n is decremented by 1 (Step S11), and it is judged whether the image ID number n reached to 1 (n=1) (Step S11). If the image ID number n does not reach 1 (Step S11, No), Steps S9 and S10 are repeated. By converting correction for each of the display gradations of the images starting from the reference image 3 in order until image 1 in an adjoining direction of an upper side of the reference image 3, it can arrange the ROI display gradations for the images 1 and 2, located on an upper side of the reference image 3 so as to make the ROI display gradation relatively uniform for the reference image 3.

By successively performing the gradation correcting process, like this, from the reference image to both of an upper and a lower direction in order, each of the display gradations for the same inspecting portion surrounded by ROIs can be arranged in overlapped portions. Consequently, when a continuous image is generated by pasting the plurality of images of the corrected display gradations, the entire continuous image can be arranged in a relatively uniform gradation while reducing the density difference at the pasting boundaries.

Figure 16:
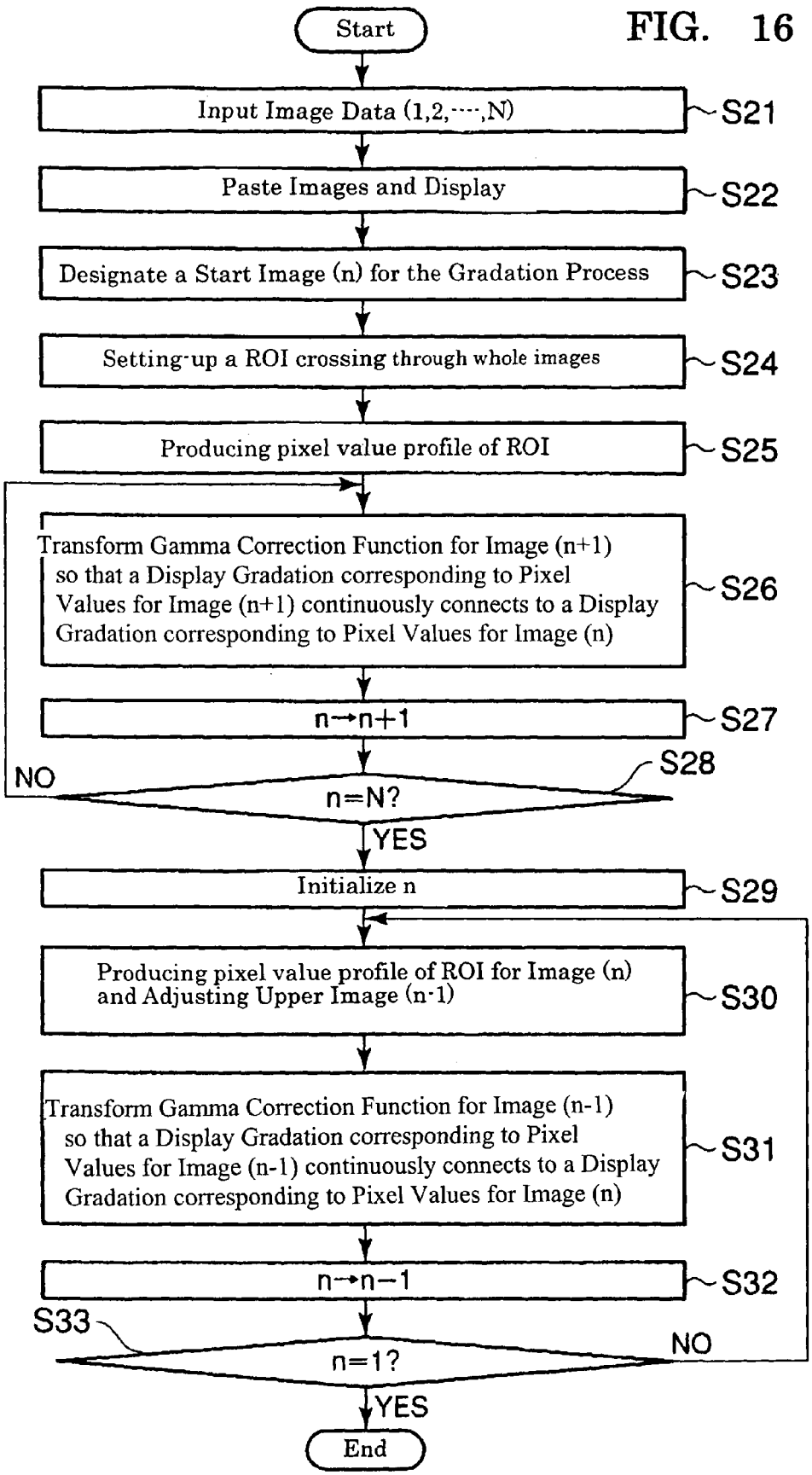
FIG. 16 is a flowchart illustrating another pasting process for generating a continuous image in a digital image processing apparatus according to the present invention.

FIG. 16 illustrates another embodiment of the gradation adjusting process consistent with the invention for adjusting gradations for a plurality of images into a relatively uniform gradation. Initially, a plurality of consecutive X-ray image data 1,2, . . . , N for using a pasting operation is input into the image memory 30 (Step S21). After initially processing in the pre-processing unit 31, the plurality of X-ray image data is processed in the gradation processing unit 37. Then, by pasting the plurality of X-ray images, a continuous image is displayed as a list on the monitor 19 (Step S22). Through input equipment 32, a reference X-ray image (n) as a starting point for the relative uniform gradations adjusting process is designated among the listed consecutive images (step S21). Next, a pixel value profile measuring ROI that vertically crosses all of the consecutive images 1 to N is established or set up through the input equipment 32 (Step S24).

Figure 17:
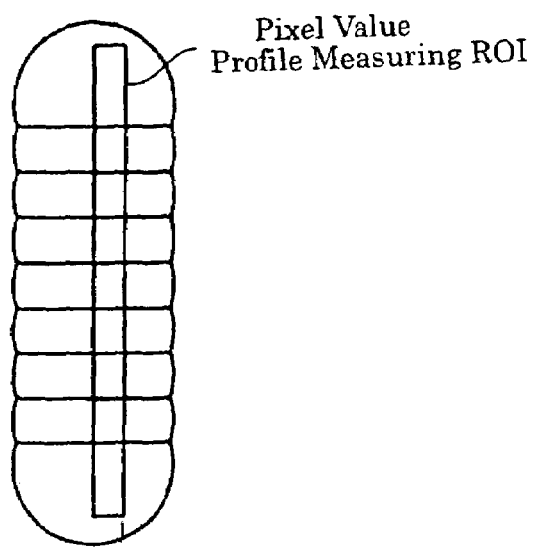
FIG. 17 is a schematic illustration for explaining an embodiment for setting up a region of interest (ROI) crossing through all the images for use at Step S24 in FIG. 16.

FIG. 17 illustrates an example for setting up the pixel value profile measuring ROI for vertically crossing all of the images 1 to N. This pixel value profile measuring ROI is established on an inspecting portion. For example, in a case of lower legs angiography, the pixel value profile measuring ROI is set up on the artery of legs. Generally, the long axis of the pixel value profile measuring ROI is arranged in parallel to a vertical axis of the images. It is also possible to voluntarily incline the ROI along a direction of the artery. Further, it is possible to voluntarily adjust a width of the pixel value profile measuring ROI, so long as the width covers a satisfactory amount of the pixels.

Setting up the ROI longitudinally to cross all of the images can be performed through input equipment, such as a mouse. It is also possible to be automatically set up by a ROI setting unit 33 (FIG. 7) by preliminarily presetting parameters for deciding the position, shape, and size of the ROI longitudinally crossing the images. For example, in the case of imaging both legs at the some time for the lower legs angiography, each longitudinal ROI is set up on a leg so as to slightly shift along the inclination of the leg in order to smoothly connect each image density for a plurality of portions for the leg. Although an attenuating filter is usually provided between the legs for avoiding the effects of X-rays directly incident on the detector, it is still possible that the amount of direct X-ray exceeds the amount of X-rays penetrated through legs. In such a case, it is possible to set up the longitudinal ROI by detecting a pixel value for leg portions, since the value for leg portions is lower than the pixel value for other portions.

Figure 18:
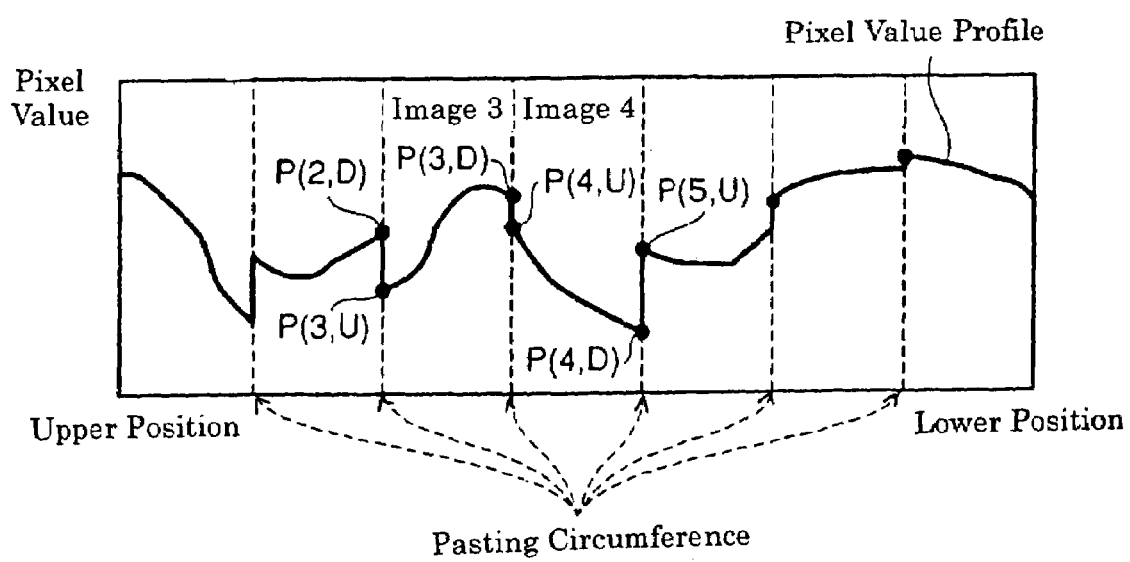
FIG. 18 is a graph for explaining an example of the pixel value profiles produced at Step S25 in FIG. 16.
Figure 19:
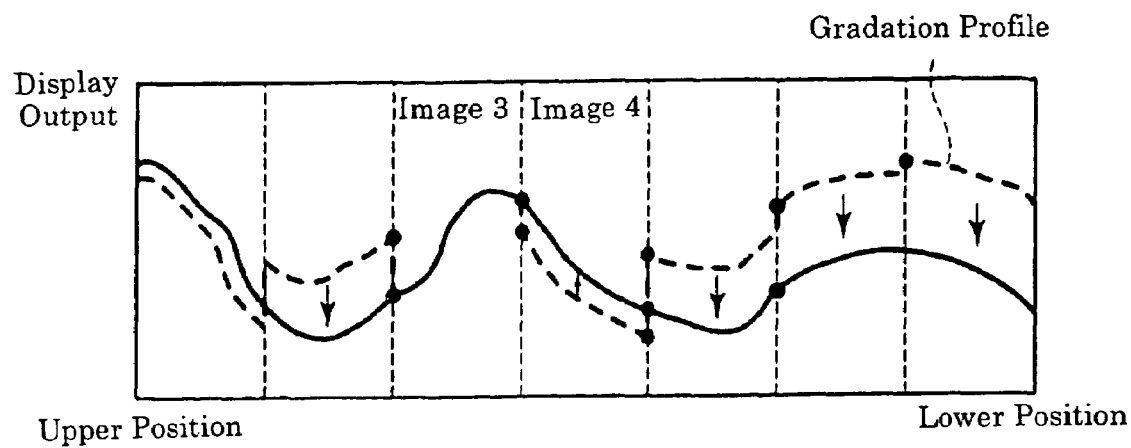
FIG. 19 is a graph for explaining an embodiment for transforming the gamma function of divisional images so as that each display gradation profile, corresponding to each pixel value profile, is continuously connected.

Next, the index value calculator 34 generates a pixel value profile for the longitudinal ROI (Step S25). At first, as to the pixel in the longitudinal ROI, an image average value of the pixel value in a traverse direction of the image is calculated. The calculated average value is distributed along a longitudinal axis. Typically, as illustrated in FIG. 18, the pixel value profile becomes discontinuous at each of pasting boundary lines. From such a discontinuous pixel value profile, each input/output relation of the gradation profile is successively corrected or adjusted based on the reference image so as to produce a continuously connected display gradation profile, such as illustrated in FIG. 19.

Initially, a gamma correcting function of the image n+1 is transformed so as that a display gradation corresponding to the pixel value of the image n+1 is continuously connected to a display gradation corresponding to the pixel value for the reference image n (Step S26, FIG. 16). In this embodiment consistent with the invention, an input/output relation, e.g., a gamma correcting function, for a gradation process corresponding to the image 4 is corrected so as that a display gradation corresponding to a pixel value P (4, U) for an upper end of image 4 adjoining the lower side of the image 3 may coincide with the display gradation corresponding to a pixel value P (3, D) at a lower end of the reference image 3. Similar to the above-described method for correcting gradations, it is also possible to convert a pixel value profile for image 4 by fixing a gamma correcting function for the image 4 so as that an input value, i.e., a pixel value P (4, U) at an upper end of the image 4, may become the pixel value P (3, D) at a lower end of the reference image 3. The gradation processing unit 37 converts the display gradations for all pixel values of the image 4 in accordance with the corrected gradation process.

Next, the image ID number n is incremented by 1 (Step S27). Then, it is judged whether the image ID number n reaches to N, i.e., n=N (Step S28). If not (Step S28, No), the process goes back to Step S26. Thus, as similar to the above explained process, a gamma correcting function for image 5 is corrected so as that a display gradation corresponding to a pixel value profile P (5, U) at an upper end of image 5 adjoining to a lower side of the image 4 may coincide to the display gradation corresponding to the pixel value P (4, D) at a lower end of the image 4. The gradation processing unit 37 converts all pixel values for the image 5 into the display gradation in accordance with the transformed gamma correcting function.

In order to successively perform gradation corrections in an upward direction from the reference image n, the reference image number n is initialized (Step S29). Similar to the above explained process, the index value calculator 34 generates each pixel value profile for the longitudinal ROI of the reference image n and an upward image n−1 adjoining the image n (Step S30). A gamma correcting function of the image n−1 is transformed so that a display gradation corresponding to the pixel values of the image n−1 is continuously connected to a display gradation corresponding to the pixel values for the reference image n (Step S31). Next, the image ID number n is decremented by 1 (Step S32). It is judged whether the image ID number n reaches 1, i.e., n=1 (Step S33). If not (Step S33 No), the process goes back to Step S30. As explained above, by successively correcting display gradation conversion in both downward and upward directions starting from the reference image, display gradations can be continuously connected from image 1 to image N as illustrated in FIG. 19.

Figure 20:
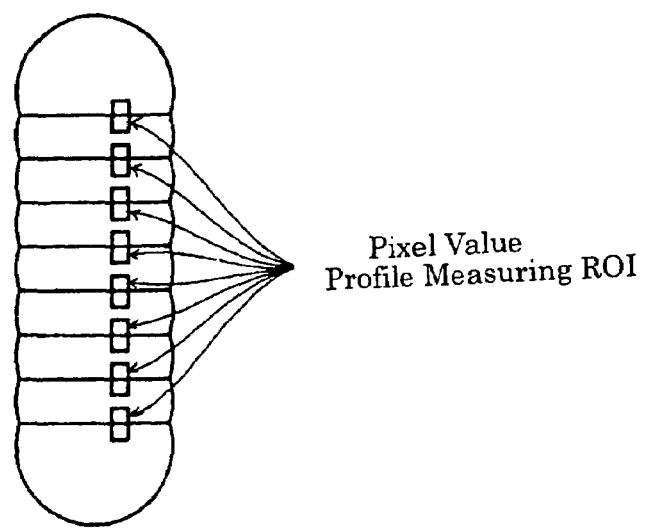
FIG. 20 is a schematic illustration for explaining another embodiment of the pixel value profile measuring ROI set up in the continuous image processing method shown in FIG. 16.

It is possible to install the above explained two types of gradation correction processes in the digital image processing unit 18 for selective use in accordance with an instruction from an operator. Further, instead of (or in conjunction with) using such a longitudinal ROI crossing all the images, it is also possible to set up a plurality of small sized pixel value profile measuring ROIs as illustrated in FIG. 20 so as that each of the small sized pixel value profile measuring ROIs crosses each of the pasting boundary lines. Even with such a small pixel value profile measuring ROI, it is possible to obtain an upper end value and a lower end value of the pixel value profile for the respective images. Accordingly, similar to the process explained above, it can correct the gradations. Of course, it is possible to set up such a plurality of small sized pixel value profile measuring ROIs in a straight line or a curved line positioned along a curve of an examining body. Further, a plurality of lines of the pixel value profile measuring ROI can be set up.

Further, it is possible to perform the gradation process by combining the above-mentioned gradation correction process using pixel value profiles corresponding to an upper end value and a lower end value for the respective images and inclinations for the respective pixel value profile so that the pixel value profile may coincide with the inclination. Thus, as illustrated in FIG. 12, pixel values are coincided by a parallel shift of the gamma correcting function. Further, as illustrated in FIG. 13, the inclinations also are coincided by expanding in a direction of the input axis. In lower legs angiography, it is also possible to divide the image into a right half image and a left half image in order to calculate an upper end value and a lower end value for the respective image areas after obtaining a pixel value or an inclination of the pixel value for each of the legs.

Figure 21:
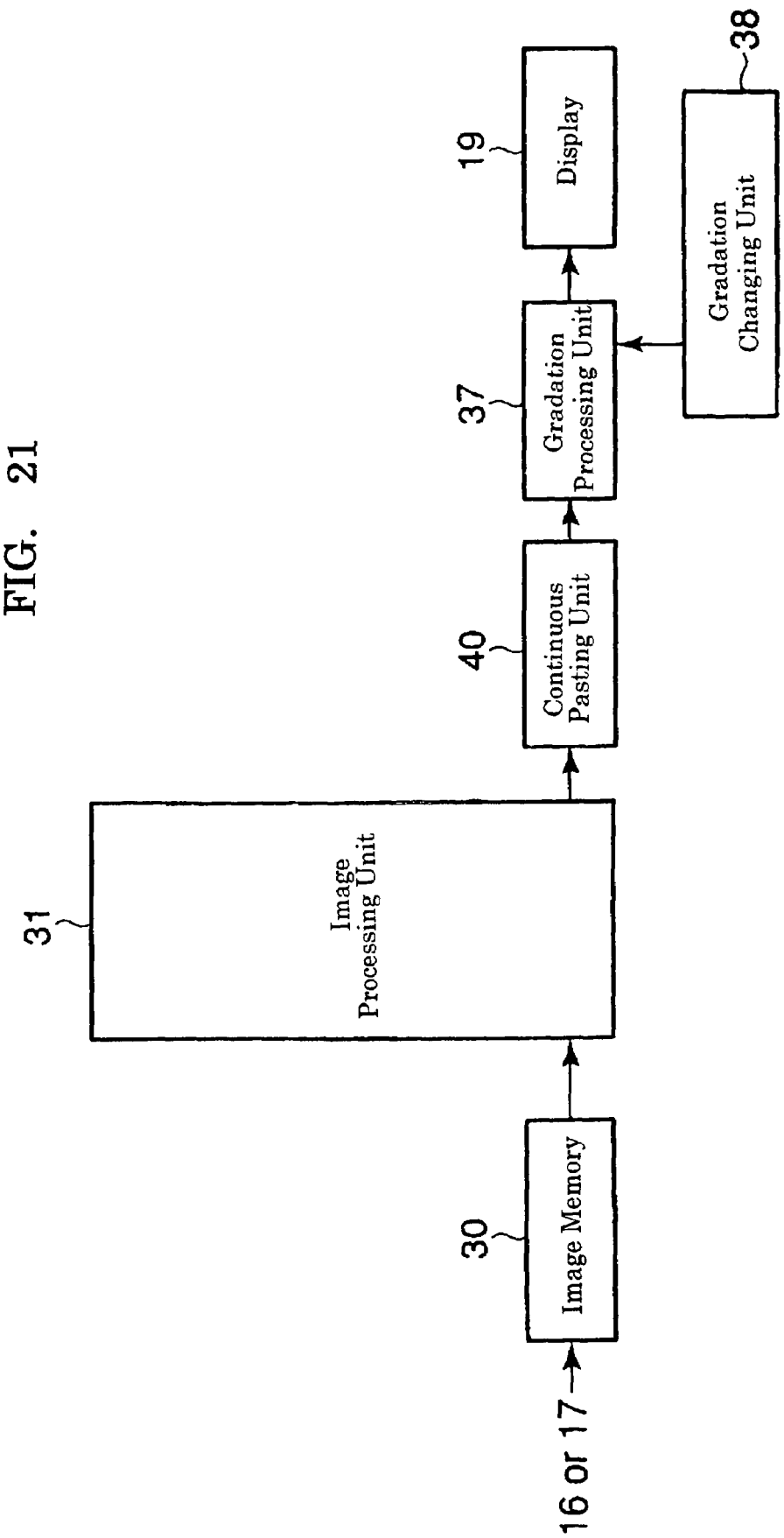
FIG. 21 is a block diagram illustrating features of another embodiment of the digital image processing apparatus of the present invention.

FIG. 21 illustrates another embodiment of the digital image processing apparatus 18. Thus, the digital image processing apparatus 18 includes an image memory 30, an image processing unit 31, a continuous pasting unit 40, a gradation processing unit 37, and an external gradation changing unit 38. This digital image processing apparatus 18 can smoothly connect display gradations for a plurality of consecutive images by unifying the input/output relation of a display gradation or a gradation profile for all the images. As a pasting method, this embodiment composes a pixel value for an adjoining image in an overlapped portion, as illustrated in FIG. 8.

The continuous pasting unit 40 composes a pixel value for two adjoining X-ray images in the overlapped portion by a weighted addition. The added value is used as a pixel value corresponding to a continuous image. The pixel value of the overlapped portion in the continuous image is obtained by the following equation.

$(a) \times$(pixel value of image $n$)$+(1-a) \times$(pixel value of image $n+1$)

Here, the weighting coefficient a is continuously, or by steps, varied between $0 \leq a \leq 1$, from an edge portion of image n to an edge portion of image n+1. The variation pattern of the weighting coefficient a may be a straight line or a curved line. For the non-overlapped portions, a pixel value for a single image is allotted as a pixel value corresponding to a continuous image. Thus, for the non-overlapped portion, a weighting coefficient 1 is given for the image. According to this method, the display gradation for image n gradually moves to the display gradation for the next image n+1. Consequently, display gradation in the overlapped region can avoid a sharp variation.

In either method explained above, since the pixel value is reduced at the periphery of a frame, it is possible to arrange its density accurately by combining a shading correction process due to a reduction of error element for the gradation calculation.

Usually, in the stepping method, a plurality of frames are imaged at each stopped position. To control the imaging X-ray amount, a first radiation is performed based on pixel value data around a center portion of an image at each stopped position. After a second radiation, a correction is added to control the X-ray amount to reduce the gap of pixel values at a pasting boundary line between the image and an image at a previous stage by adding pixel value data in the ROI obtained by the previously explained methods to the image data for the first radiation. The above explained first and second methods can increase accuracy for adjustment by reducing the gradation adjusting amount for the respective images. The third method can obtain a continuous image suitable for inspection by reducing variations of pixel values among the respective images.

As explained above, the apparatus and method for processing X-ray images of the present invention can obtain a relatively uniform density of a continuous image while eliminating variations of density for a plurality consecutive images. Further, the apparatus and method for processing X-ray images of the present invention can obtain a relatively uniform density of a continuous image by reducing the operation load for adjusting display gradations among the plurality of consecutive images. Thus, the apparatus and method for processing X-ray images consistent with the present invention can obtain a continuous image suitable for inspection.

This invention is not limited to the embodiments as explained above, but can be performed by various modifications. For example, it is possible to use a detector having a rectangular light receiving surface, instead of using a circular light receiving surface for the detector. Further, it is possible to combine or delete some of the functional units in the disclosed embodiments.

The invention claimed is:

1. An X-ray image processing device configured to obtain a plurality of consecutive divisional X-ray images along a longitudinal axis of an examined body, each of the divisional X-ray images overlapping with one or more adjoining X-ray images of the other consecutive divisional X-ray images along a direction in which the divisional X-ray images were obtained, the X-ray image processing device, comprising:
   a memory configured to store X-ray image data of the plurality of consecutive divisional X-ray images, the X-ray image data including pixel values;
   an ROI setting unit configured to establish a region of interest (ROI) around an edge line disposed through a center of an overlapping portion between a reference image and an adjoining X-ray image that is read out from the memory, the ROI being less than the entire overlapping portion and including portions of both the reference image and the adjoining X-ray image;
   an index value calculator configured to determine, for each of the overlapped edge portions, an index value based on the pixel values within the ROI;
   a gradation calculator configured to determine display gradations for the image data of the adjoining X-ray images, based on the index value;
   a gradation processing unit configured to correct the pixel values for the X-ray image data so that the display gradations of the image data of the adjoining X-ray images substantially coincides; and
   a continuous pasting operation unit configured to generate a continuous image by pasting together the X-ray image data of the altered pixel values.

2. The X-ray image processing device according to claim 1, wherein, the index value is selected from the group consisting of:
   a mean pixel value within the ROI, a maximum pixel value within the ROI, a minimum pixel value within the ROI, a center pixel value within the ROI, and the most frequent pixel value in the ROI.

3. The X-ray image processing device according to claim 1, wherein the index value calculator is configured to determine the index value based on a histogram of pixel values within the ROI.

4. The X-ray image processing device according to claim 1, wherein the index value calculator is further configured to derive the index value from a reference image corresponding to one of the divisional X-ray images, and wherein the gradation processing unit is configured to successively correct the display gradations so that the display gradations substantially correspond to the index value.

5. The X-ray image processing device according to claim 4, wherein the gradation processing unit is configured to successively correct the display gradations for the adjoining images by shifting a correction function so as to correspond to the gradation of the reference image.

6. The X-ray image processing device according to claim 5, wherein the correction function is a gamma correcting function which is performed by successively correcting the displayed gradations for the adjoining images by shifting a correction function so as to correspond to the gradation of the reference image.

7. The X-ray image processing device according to claim 6, wherein the gradation processing unit is configured to generate the gamma correcting function for each of the adjoining images by expanding the gamma correcting function for the reference image based on a ratio of the respective index value of an adjoining image to the index value of the reference image.

8. The X-ray image processing device according to claim 1, wherein the gradation processing unit is configured to apply a gamma correcting function to the adjoining images such that a minimum pixel value and an average pixel value obtained at the upper ROI of each of the adjoining images coincides to a minimum pixel value and an average pixel value obtained at the lower ROI of the reference image.

9. An X-ray image processing system for generating a continuous image from a plurality of consecutive divisional X-ray images obtained along a longitudinal axis of an examined body, each of the divisional X-ray images having one or more edge portions overlapped with one or more edge portions of adjoining images of the other divisional X-ray images, and for performing correcting operations on display gradations of the images, the X-ray images processing system comprising;
   a memory configured to store image data of the divisional X-ray images;
   a region of interest (ROI) setting unit configured to establish at least one ROI around a edge line disposed through a center of the overlapping edge portions of the divisional X-ray images, the at least one ROI including portions of each of the divisional X-ray images;
   a profile forming unit configured to provide, for each of the divisional X-ray images, a pixel value profile of pixels within the ROI;
   a gradation processing unit configured to successively correct each of the display gradations for the divisional X-ray images so as to continuously match (A) the display gradation corresponding to the pixel value profile of a reference image among the divisional X-ray images to (B) the display gradation corresponding to the pixel value profile of a divisional image adjoining the reference image; and a continuous image processing unit configured to generate a continuous image by pasting together the plurality of divisional X-ray images having respective corrected display gradations.

10. The X-ray image processing system according to claim 9, wherein the profile forming unit is configured to determine an average value of the pixels along a horizontal direction of the ROI for the plurality of X-ray images.

11. The X-ray image processing system according to claim 9, wherein the gradation processing unit applies a gamma correcting function to the divisional X-ray images adjoining the reference image so that the respective pixel value profile of each of the adjoining images substantially matches a pixel value profile of the reference image.

12. The X-ray image processing system according to claim 9, wherein the setting unit is configured to establish a plurality of small ROIs, each small ROI crossing over a respective one of the pasting boundary lines of the divisional X-ray images.

13. The X-ray image processing system according to claim 12, wherein the ROI setting unit is configured to establish the small ROIs along a straight line or a curved line.

14. The X-ray image processing system according to claim 11, wherein the gradation processing unit is configured to correct the display gradations so that a slope at a lower end value of the pixel value profile of each adjoining image coincides to a slope at an upper end value of the pixel value profile of the reference image.

15. The X-ray image processing system according to claim 9, wherein the continuous image processing unit is configured to vary a weighting coefficient for calculating a weighted average between pixel values of two of the adjoining images in an overlapped portion of the two adjoining images.

16. The X-ray image processing system according to claim 15, wherein the weighting coefficient at the overlapped portion of X-ray images varies linearly or non-linearly.

17. An X-ray image processing method configured to obtain a plurality of consecutive divisional X-ray images along a longitudinal axis of an examined body, each of the divisional X-ray images overlapping with one or more adjoining X-ray images of the other consecutive divisional X-ray images along a direction in which the divisional X-ray images were obtained, the X-ray image processing method, comprising:
   storing X-ray image data of consecutive divisional X-ray images in a memory;
   establishing a region of interest (ROI) around an edge line disposed through a center of an overlapping portion between a reference image and an adjoining image that is read out from the memory, the ROI being less than the entire overlapping portion and including portions of both the reference image and the adjoining X-ray image;
   determining, for each overlapped edge portion of the divisional X-ray images, an index value, based on the pixel values within the corresponding ROI;
   determining display gradations for the X-ray images, based on the corresponding index values;
   correcting the pixel values for the X-ray images so that the display gradations of the adjoining images are substantially uniform; and
   generating a continuous image of substantially uniform display gradations by pasting together the divisional X-ray images with corrected display gradations.

18. The method for processing X-ray images according to claim 17, wherein the index value is selected from the group consisting of: a mean pixel value, a maximum pixel value, a minimum pixel value, a center pixel value, and the most frequent pixel value in the ROI.

19. The method for processing X-ray images according to claim 17, wherein determining the index value comprises determining the index value based on a histogram of pixel values within the ROI.

20. The method for processing X-ray images according to claim 17, wherein determining the index value comprises deriving the index value from a reference image among the divisional X-ray images; and
   determining the display gradations comprises successively correcting the display gradations so that the display gradations substantially correspond to the index value.

21. The method for processing X-ray images according to claim 20, wherein successively performing corrections comprises: shifting a correcting function used to correct the reference image.

22. The method for processing X-ray images according to claim 21, wherein the correcting function comprises a gamma correcting function.

23. The method for processing X-ray images according to claim 22, further comprising generating the gamma correcting function for each of the adjoining images by expanding the gamma correcting function for the reference image based on a ratio of the respective index value of the adjoining image to the index value of the reference image.

24. The method for processing X-ray images according to claim 21, wherein the index value of the adjacent image is selected from the group consisting of:
   a minimum pixel value and an average pixel value, obtained at an upper side ROI of the adjoining image; and
   the index value of the reference image is selected from the group consisting of a minimum pixel value and an average pixel value, obtained at a lower side ROI of the reference image.

25. A method for processing X-ray images, comprising:
   storing in memory a plurality of X-ray image data corresponding to a plurality of consecutive divisional X-ray images;
   establishing at least one region of interest (ROI) around a edge line disposed through a center of overlapping edge portions of the divisional X-ray images, the at least one ROI including portions of each of the divisional X-ray images;
   generating, for each of the divisional X-ray images, a pixel value profile of pixels within the ROI;
   successively correcting display gradations respectively for each of the divisional X-ray images so as to continuously match (A) the display gradation corresponding to the pixel value profile for a reference image among the divisional X-ray images to (B) the display gradation corresponding to the pixel value profile of a divisional X-ray image adjoining the reference image; and
   generating a continuous image by pasting together the divisional X-ray images having respective corrected display gradations.

26. The method for processing X-ray images according to claim 25, wherein the index value comprises as an average value of the pixel value profile along a horizontal direction of the corresponding ROI.

27. The method for processing X-ray images according to claim 25, further comprising
   applying a gamma correcting function to the divisional X-ray images adjoining the reference image so that the respective pixel value profile of each of the adjoining images continuously matches a pixel value profile of the reference image.

28. The method for processing X-ray images according to claim 25, wherein establishing at least one ROI comprises establishing a plurality of small ROIs, each of the small ROIs crossing over a respective one of the pasting boundary lines of the divisional X-ray images.

29. The method for processing X-ray images according to claim 25, wherein establishing the plurality of small ROIs comprises establishing the plurality of small ROIs along a straight line or a curved line in the longitudinal direction.

30. The method for processing X-ray images according to claim 25, wherein the further comprising
correcting the display gradations so that a slope at a lower end value of the pixel value profile of each adjoining image coincides to a slope at an upper end value of the pixel value profile of the reference image.

31. The method for processing X-ray images according to claim 25, further comprising
generating weighting coefficient for determining a weighted average of pixel values in an overlapping area of two adjoining X-ray images, the weighted average being varied.

32. The method for processing X-ray images according to claim 31, wherein the weighting coefficient varies linearly or non-linearly.

* * * * *